United States Patent
Tsuji et al.

(10) Patent No.: US 7,275,006 B2
(45) Date of Patent: Sep. 25, 2007

(54) WORKPIECE INSPECTION APPARATUS ASSISTING DEVICE, WORKPIECE INSPECTION METHOD AND COMPUTER-READABLE RECORDING MEDIA STORING PROGRAM THEREFOR

(75) Inventors: Yoshitake Tsuji, Kanagawa (JP); Yasuko Saito, Kanagawa (JP); Hideo Tsuchiya, Kanagawa (JP)

(73) Assignee: Advanced Mask Inspection Technology Inc., Yokohama-shi (JP)

( * ) Notice: Subject to any disclaimer, the term of this patent is extended or adjusted under 35 U.S.C. 154(b) by 0 days.

(21) Appl. No.: 11/265,180

(22) Filed: Nov. 3, 2005

(65) Prior Publication Data

US 2007/0055467 A1 Mar. 8, 2007

(30) Foreign Application Priority Data

Sep. 6, 2005 (JP) ............................. 2005-257605

(51) Int. Cl.
*G01N 37/00* (2006.01)

(52) U.S. Cl. ........................................... 702/81
(58) Field of Classification Search ................ 702/81, 702/82, 83, 84, 35, 36; 438/14, 16; 382/141, 382/145, 149
See application file for complete search history.

(56) References Cited

U.S. PATENT DOCUMENTS

| | | | |
|---|---|---|---|
| 5,563,702 A | 10/1996 | Emery et al. | |
| 2003/0007677 A1* | 1/2003 | Hiroi et al. | 382/149 |
| 2004/0126005 A1* | 7/2004 | Duvdevani et al. | 382/149 |

FOREIGN PATENT DOCUMENTS

| | | |
|---|---|---|
| JP | 8-76359 | 3/1996 |
| JP | 10-142771 | 5/1998 |
| JP | 2004-191957 | 7/2004 |

* cited by examiner

*Primary Examiner*—John Barlow
*Assistant Examiner*—Xiuqin Sun
(74) *Attorney, Agent, or Firm*—Oblon, Spivak, McClelland, Maier & Neustadt, P.C.

(57) ABSTRACT

An assistance device of workpiece inspection apparatus embodying this invention includes a regional image data conversion unit which inputs region data indicative of a specified region of a workpiece being tested with a pattern formed thereon, and then converts the data to regional image data. The device also includes a data distribution processing unit which distributes the regional image data for output to the workpiece inspection apparatus in conformity with an inspection processing speed of the external workpiece inspection apparatus, which performs pattern defect inspection while comparing optical image data of the workpiece to prespecified reference image data.

4 Claims, 16 Drawing Sheets

WORKPIECE INSPECTION APPARATUS ASSISTING DEVICE, WORKPIECE INSPECTION METHOD AND COMPUTER-READABLE RECORDING MEDIA STORING PROGRAM THEREFOR

CROSS-REFERENCE TO RELATED APPLICATION

This application is based upon and claims the benefit of priority from prior Japanese Patent Application No. 2005-257605, filed on Sep. 6, 2005, the entire contents of which are incorporated herein by reference.

BACKGROUND OF THE INVENTION

1. Field of the Invention

The present invention relates to workpiece inspection apparatus and method and also to a software program for causing computers to execute the method. More particularly but not exclusively, this invention relates to pattern inspection technologies for inspection of pattern defects of a test object, such as a workpiece in the manufacture of semiconductor devices. The invention also relates to apparatus for inspecting ultrafine pattern defects of photomasks, wafers, liquid crystal substrates or else for use in fabrication of semiconductor devices and liquid crystal display (LCD) panels.

2. Description of the Related Art

In recent years, with the quest for higher integration and larger capacity of large-scale integrated (LSI) circuits, semiconductor devices are becoming narrower in circuit linewidth required. These semiconductor devices are fabricated by using an original or "master" plate with a circuit pattern formed thereon (also called a photomask or a reticle as will be generically referred to as a mask hereinafter) in a way such that the pattern is exposure-transferred by reduced projection exposure equipment, known as a stepper, onto a target wafer to thereby form thereon a circuit. For the manufacture of a mask to be used to transfer such ultrafine circuit pattern onto wafers, pattern photolithography equipment is used, which is capable of "drawing" microcircuit patterns.

Improving manufacturing yields is inevitable for the microfabrication of LSI chips which entail increased production costs. Currently, circuit patterns of LSIs, such as 1-gigabit class dynamic random access memories (DRAMs), are on the order of nanometers (nm), rather than submicron order. One major factor for reducing yields is the accuracy of the apparatus for detecting defects, which take place in a mask pattern as used when an ultrafine pattern is exposed and transferred onto semiconductor wafers by photolithography techniques. As LSI patterns to be formed on semiconductor wafers are further miniaturized in recent years, the size dimensions that must be detected as pattern defects became much smaller than ever before. Thus, a need is felt to achieve further increased accuracy of the pattern inspection apparatus operable to inspect the mask for defects.

Incidentally, with recent advances in multimedia technologies, LCD panels are becoming larger in substrate size and finer in pattern of thin film transistors (TFTs) as formed on liquid crystal substrates. This larger/finer trend requires an ability to inspect ultrasmall pattern defects in a wide range. For this reason, it is an urgent challenge to develop an advanced workpiece inspection apparatus capable of efficiently inspecting defects of photomasks in a short time period, which are for use in the manufacture of such large-area LCD patterns and large-screen LCD panels.

An ordinary approach to performing inspection in prior known pattern inspection apparatus is to compare an optical image resulted from the image sensing of a pattern formed on a workpiece such as a mask at a specified magnification to design data or, alternatively, compare it to a sensed optical image of an identical pattern on the workpiece in a way as disclosed, for example, in Published Japanese Patent Application No. 8-76359 ("JP-A-8-76359"). An example of pattern inspection methodology is the so-called "die to die" inspection method for comparing optical image data obtained by image pickup of identical patterns at different locations on the same mask. Another example is a "die to database" inspection method having the steps of receiving computer-aided design (CAD) data indicative of a designed pattern, converting the CAD data into graphics data (i.e., design pattern data) with an appropriate format for input to photolithography equipment, inputting the data to an inspection apparatus, generating design image data (reference image data) based on the input data, and then comparing it to optical image data, that is, measurement data resulting from the image pickup of a target pattern being tested. The inspection method for use in such apparatus, the workpiece is mounted on a stage, which moves to permit light rays to scan a surface of the workpiece for execution of the intended inspection. A light source and its associated illumination optical lens assembly are used to emit and guide the light to fall onto the workpiece. The light that passed through the workpiece or reflected therefrom travels via the optics to enter a sensor so that a focussed optical image is formed thereon. This optical image is sensed by the sensor and then converted to electrical measurement data, which will be sent to a comparator circuit. After position-alignment between images, the comparator circuit compares the measured data to reference image data in accordance with an adequate algorithm. If these fail to be matched, then determine that pattern defects are present.

The linewidth of design pattern data becomes finer in recent years. In addition, due to the presence of micropatterns for the optical proximity correction (OPC) use, it becomes more difficult to match together the design image data and the optical image data for use as measured data. This difficulty can often lead to inspection errors—that is, those that are inherently not judged as defects are erroneously regarded as defects, known as false or "pseudo" defects. One approach to avoiding this problem is to "loosen" a decision threshold as used in the comparator circuit. Unfortunately, this approach does not come without accompanying a penalty which follows: the to-be-detected size accuracy is lowered, resulting in that any defects in the required pattern are no longer detectable. Thus it is required to apply comparison inspection to the "imaged" pattern at certain level of inspection accuracy as selected from a plurality of predefined ranks of accuracy on a case-by-case basis.

A technique for performing the comparison inspection while categorizing graphics patterns into a plurality of ranks is disclosed, for example, in JP-A-2004-191957 and JP-A-10-142771. However, these Japanese patent documents fail to teach any practically implementable scheme for categorizing graphic patterns in multiple ranks to enable realization in the apparatus, which is deemed impractical and deficient from a viewpoint of practicability. Thus it is demanded to attain a solving technique thereof.

It is an ordinary approach that in case defects are found in the workpiece of interest, defect reviewing is carried out by a user. However, when the above-described OPC-based micropatterns are diversified, inherently defect-free patterns can be misjudged as defective ones, causing user-executed defect review workload to go beyond the limit in terms of the time required. This in turn poses a problem as to redoing of the inspection per se in cases where a large number of pseudo-defects, such as those stated above, appear within the workpiece. Alternatively, a problem arises as to a need to prepare again the high-priced workpiece itself. Adversely, the decision threshold is loosened, there was a drawback concerning the lack of an ability to detect defects in a pattern which is under strict size accuracy requirements. Furthermore, from viewpoints of avoiding unwanted increases in scale and complexity of inspection equipment along with cost rise-up and development period prolongation, a need is also felt to minimize amelioration of the currently existing inspection apparatus for overcoming the problems stated above.

BRIEF SUMMARY OF THE INVENTION

It is an object of the present invention to provide a method and apparatus capable of avoiding the problems above and performing workpiece inspection at appropriate accuracy.

In accordance with one aspect of this invention, an assisting device of a workpiece inspection apparatus includes a regional image data conversion unit which is operable to input region data indicative of a specified region of a workpiece being tested with a pattern formed thereon and then convert the data to regional image data, and a data distribution processing unit for distribution of the regional image data to thereby output to the workpiece inspection apparatus in conformity with an inspection processing speed of the external workpiece inspection apparatus, which performs pattern defect inspection while comparing optical image data of the workpiece to specified reference image data.

In accordance with another aspect of the invention, an assisting device of a workpiece inspection apparatus includes a region data conversion unit operative to input region data indicative of a specified region of a workpiece being tested with a pattern formed thereon and convert it to second region data being less in information amount than the region data. The device also includes a data distribution processing unit for distribution of the second region data to thereby output to the workpiece inspection apparatus in conformity with an inspection processing speed of the external workpiece inspection apparatus which performs pattern defect inspection while comparing optical image data of the workpiece to prespecified reference image data.

In accordance with a further aspect of the invention, a workpiece inspection method includes obtaining optical image data of a workpiece being tested with a pattern formed thereon, making design image data based on design pattern data for use as the source of pattern formation of the workpiece being tested, inputting, from an external device, regional image data as created based on region data indicative of a specified region of the workpiece, and using the regional image data to compare the design image data to the optical image data.

In accordance with another further aspect of the invention, there is provided a computer-readable record carrier body that stores a software program for causing a computer to execute workpiece inspection control/management in a procedure which includes the steps of first storage processing for storing in a first storage device design pattern data for use as a source of pattern formation at a workpiece being tested with a pattern formed thereon, input processing for inputting from an external device regional image data created based on region data indicative of a specified region of the test workpiece, second storage processing for storing the input regional image data in a second storage device, design image data creation processing for making design image data based on the design pattern data as stored in the first storage device, optical image data input processing for input of optical image data of the workpiece, third storage processing for storing the input optical image data in a third storage device, and comparison processing for using the regional image data to compare the design image data and the optical image data.

DETAILED DESCRIPTION OF THE INVENTION

Embodiment 1

Figure 1:
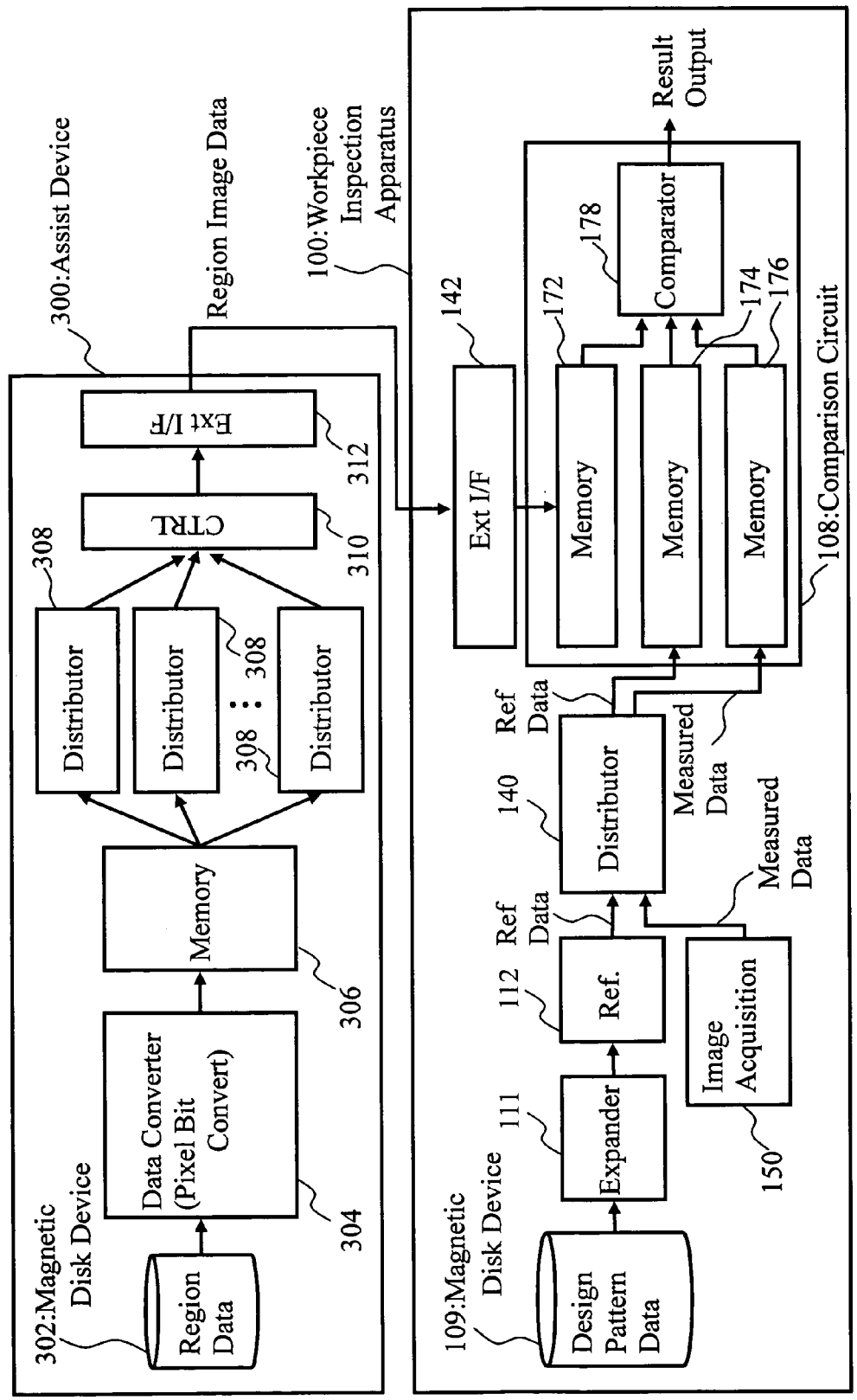
FIG. 1 is a block diagram showing a major configuration of a workpiece inspection apparatus and a support/assistance device in an embodiment 1 of the invention.

FIG. 1 is a block diagram showing a major configuration of a workpiece inspection apparatus and a support/assistance device in an embodiment 1.

In FIG. 1, the workpiece inspection apparatus is indicated by numeral 100 and is for detecting defects of a workpiece being tested, such as a photomask or wafer or else. The apparatus 100 is operatively associated with an assistance device 300. This device 300 includes a magnetic disk device 302, a data conversion processing circuit 304 which is one example of the regional image data conversion unit as claimed, a data memory 306, a parallel combination of data distribution processing circuits 308 that are an example of the data distribution processing unit, a distribution control circuit 310, and an external interface (I/F) 312. Regarding the data distribution processor circuits 308, a plurality of stages are provided. The workpiece inspection apparatus 100 includes a magnetic disk device 109, an expansion circuit 111, a reference circuit 112, an optical image acquisition unit 150, a data distribution processing circuit 140, an external I/F 142, and a comparison circuit 108. The comparator circuit 108 has a regional image memory 172, reference data memory 174, measurement data memory 176, and comparison processing circuit 178.

Figure 2:
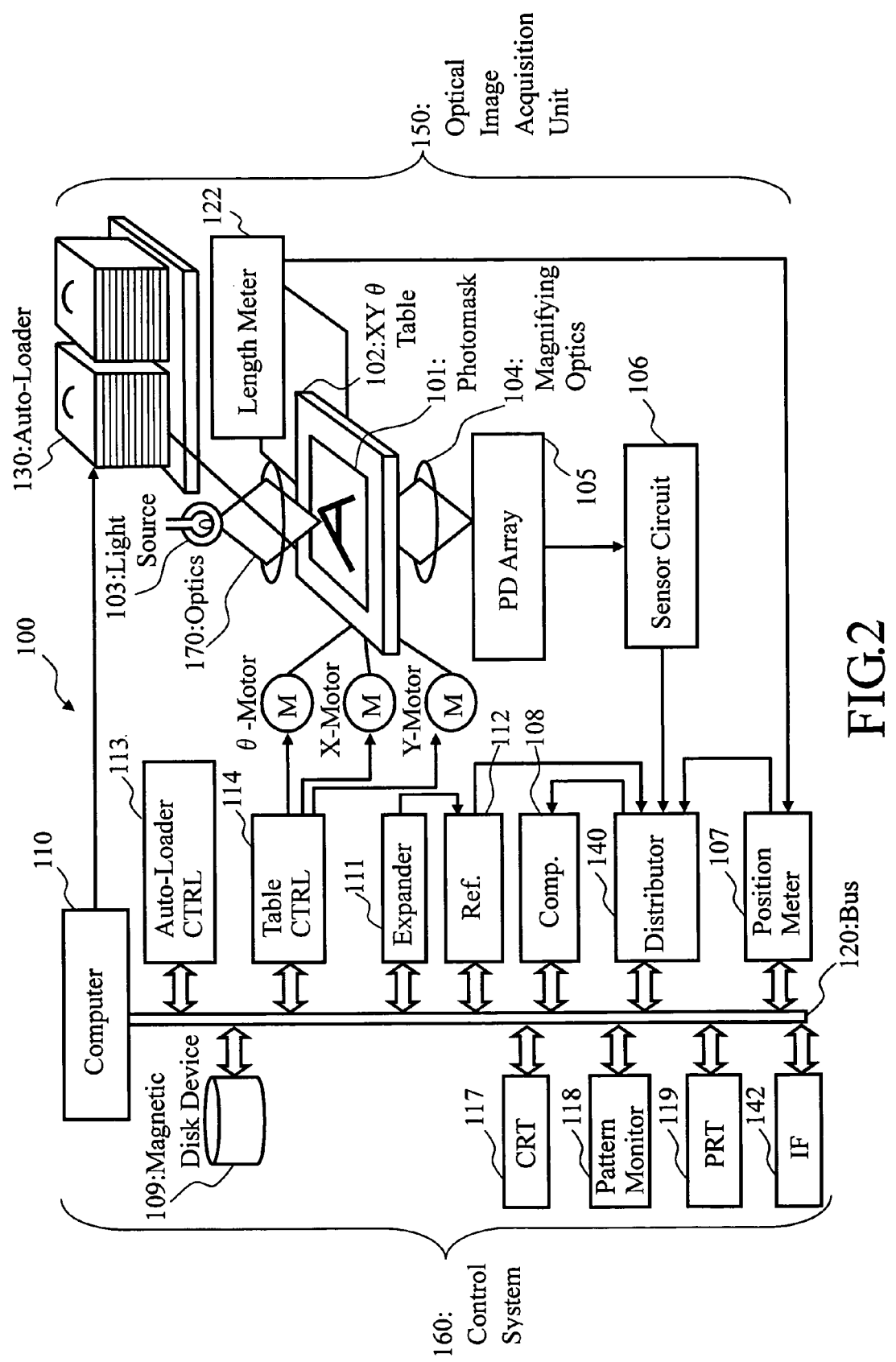
FIG. 2 illustrates an entire configuration of the workpiece inspection apparatus shown in FIG. 1.

FIG. 2 depicts an overall configuration of the workpiece inspection apparatus 100 in FIG. 1. In FIG. 2, the inspection apparatus 100 is equipped with the above-noted optical image acquisition unit 150 and a system control circuit 160. The optical image acquisition unit 150 includes an X-Y-θ table 102, light source 103, magnifying optical lens assembly 104, photodiode (PD) array 105, sensor circuit 106, laser-assisted length measurement system 122, automatic loader 130, and illumination optics 170. In the system control circuit 160, a control computer 110 is connected via a data transfer bus 120 to a position circuit 107, the comparator circuit 108 that is an example of the comparison unit, the expander circuit 111 that is one example of the design image data creation unit, a reference circuit 112, the data distribution processor circuit 140, the external I/F 142, an auto-loader control circuit 113, a table control circuit 114, the magnetic disk device 109 that is an example of the storage device, a cathode ray tube (CRT) display 117, a pattern monitor 118, and a printer 119. The XYθ table 102 is driven by an X-axis motor, Y-axis motor and θ-axis motor.

Note here that in FIGS. 1 and 2, those parts or components other than the constituent members required for the explanation of this embodiment 1 are eliminated. It would readily occur to skilled persons that the workpiece inspection apparatus 100 and assistance device 300 are designed, for practical implementation, to include other necessary arrangements.

Figure 3:
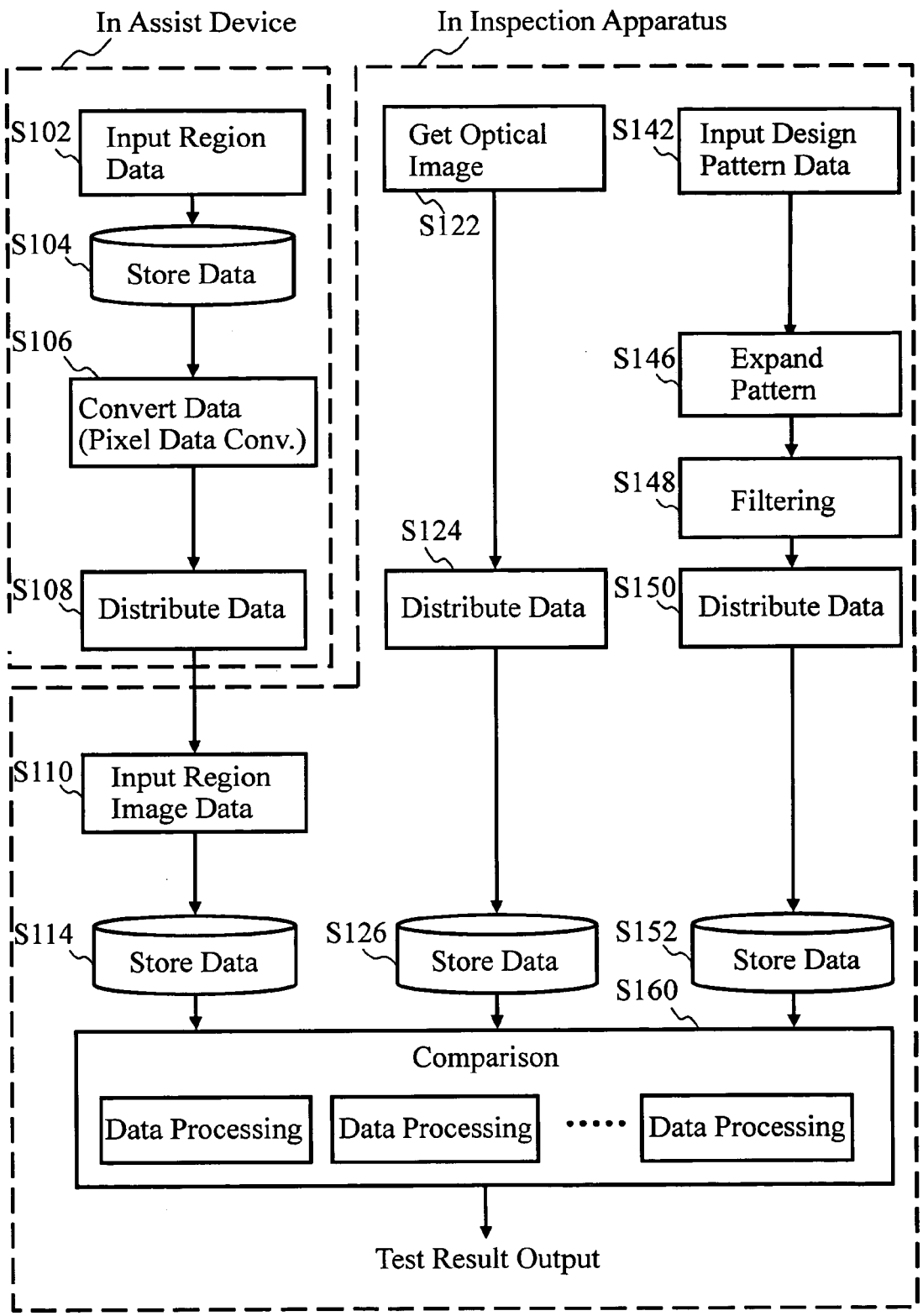
FIG. 3 is a flow chart showing some major process steps of a workpiece inspection method for use in the workpiece inspection apparatus and assistance device in the embodiment 1.

FIG. 3 is a flowchart showing some major process steps of a workpiece inspection method for use in the workpiece inspection apparatus and assistance device in the embodiment 1.

In FIG. 3, the workpiece inspection method is arranged to perform, in the assistance device 300, a series of processes at a region data input step (S102), storing step (S104), data conversion step (S106), and data distribution processing step (S108). The inspection method executes, in the workpiece inspection apparatus, a series of processes at a regional image data input step (S110), optical image acquisition step (S122), data distribution processing step (S124), storing step (S126), design pattern data input step (S142), and storing step (S144), along with a pattern expansion step (S146), filtering step (S148), data distribution processing step (S150), storage step (S152), and comparison step (S160).

At the optical image acquisition step S122, the optical image acquisition unit 150 obtains optical image data (i.e., measured data) at a photomask 101 for use as a workpiece or "sample" on which a graphic form that is indicated by graphics data contained in the design pattern data is drawn based on the design pattern data. An exemplary procedure of such optical image acquisition is as follows. The photomask 101 is mounted as a workpiece to be tested on the movably provided XYθ table 102, which is driven by the X, Y and θ-axis motors to move in horizontal and rotation directions. The photomask 101 has a pattern formed thereon, on which light is irradiated by the light source 103 of appropriate type, which is disposed over the XYθ table 102. Light rays or fluxes as emitted from the light source 103 travels via the illumination optics 170 to fall onto the photomask 101, that is, the workpiece being tested. Disposed beneath the photomask 101 are the magnifying optics 104, PD array 105 and sensor circuit 106. The light that passed through the photomask 101 for use as the workpiece, such as an exposure mask, is guided to progress through the magnifying optics 104 to hit PD array 105 so that a focussed optical image is formed thereon.

Figure 4:
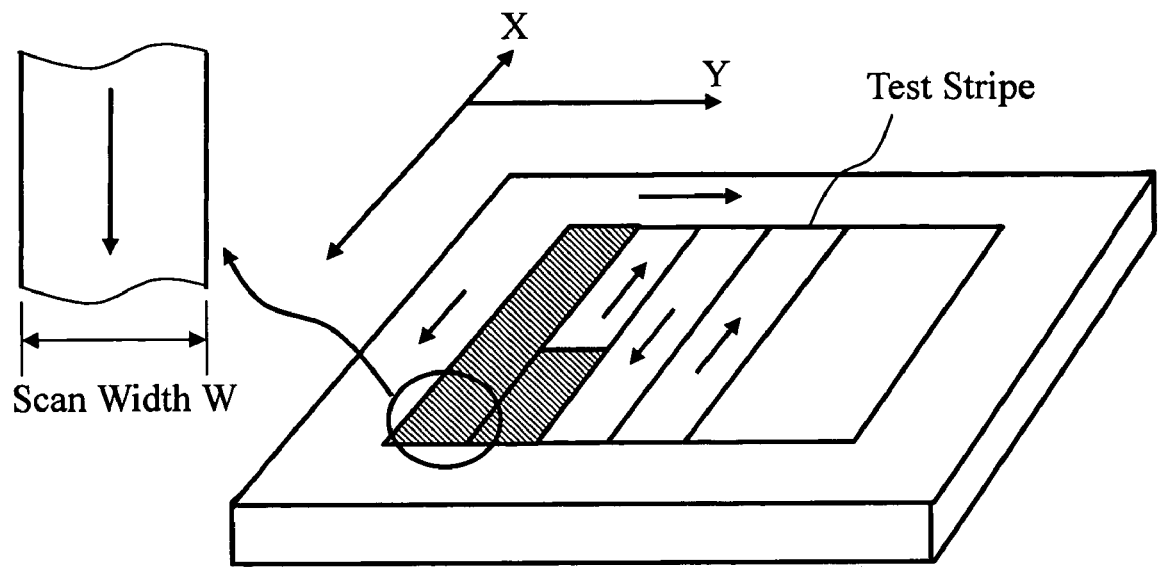
FIG. 4 is a diagram for explanation of an optical image acquisition procedure.

FIG. 4 is a diagram for explanation of the acquisition procedure of an optical image. As shown in FIG. 4, a workpiece surface area under inspection is virtually subdivided along the Y direction into a plurality of narrow, elongate test strips each having a scan width W. The XYθ table 102 is motion-controlled to permit respective divided test strips to be scanned continuously so that an optical image is acquired during movement in the X direction. The PD array 105 is operable to seamlessly input images of the scan width W such as shown in FIG. 4. Then, after having captured the image of a first test strip, obtain the image of a second test strip while moving in the opposite direction in this event so that an image of scan width W is input in a similar way. Next, in the case of getting the image of a third test strip, image capturing is done while moving in the direction opposite to that for acquisition of the second test strip image—namely, in the same direction as that for acquisition of the first test strip image. By continuously capturing images in this serpentine manner, it is possible to shorten wasteful processing times.

The image that is focussed on the PD array 105 is photoelectrically converted thereby and is then analog-to-digital (A/D) converted by the sensor circuit 106. PD array 105 has time-delay integrator (TDI) sensors installed. By causing the XYθ table 102 for use as a workpiece support stage to move continuously in the X-axis direction, the TDI sensors pick up a circuit pattern of the photomask 101, i.e., workpiece being tested. The light source 103, magnifying optics 104, PD array 105 and sensor circuit 106 make up a high-power inspection optical system.

The XYθ table 102 is driven by the table control circuit 114 under control of the control computer 110. Table 102 is movable by a drive system such as three-axis (X-Y-θ) motors for driving it in the X, Y and θ directions. Examples of these X, Y and θ motors are stepper motors. A moved position of XYθ table 102 is measured by the laser-aided length measurement system 122 to generate a measurement signal, which is supplied to the position circuit 107. The photomask 101 on XYθ table 102 is automatically transported from the auto-loader 130 that is driven by the auto-loader control circuit 113 and is then automatically educed after completion of the inspection.

Measurement data (optical image data) as output from the sensor circuit 106 is sent forth toward the data distribution processor circuit 140 along with output data of the position circuit 107 indicative of a present position of the photomask 101 on XYθ table 102. The measured data may be 8-bit signless data representing the gradation or "tone" of the brightness of each pixel.

At the data distribution step S124, the data distribution processor circuit 140 sends the input measurement data toward the comparison circuit 108 while synchronizing it with the test region for comparison with reference data to be described later.

At the storing step S126, the measurement data is sequentially sent to and temporarily stored in the measured data memory 176 within the comparator circuit 108.

At the design pattern data input step S142, the design pattern data that was used during pattern formation of the photomask 101 is stored in the magnetic disk device 109, which is an example of the storage device (storage unit).

Figure 5:
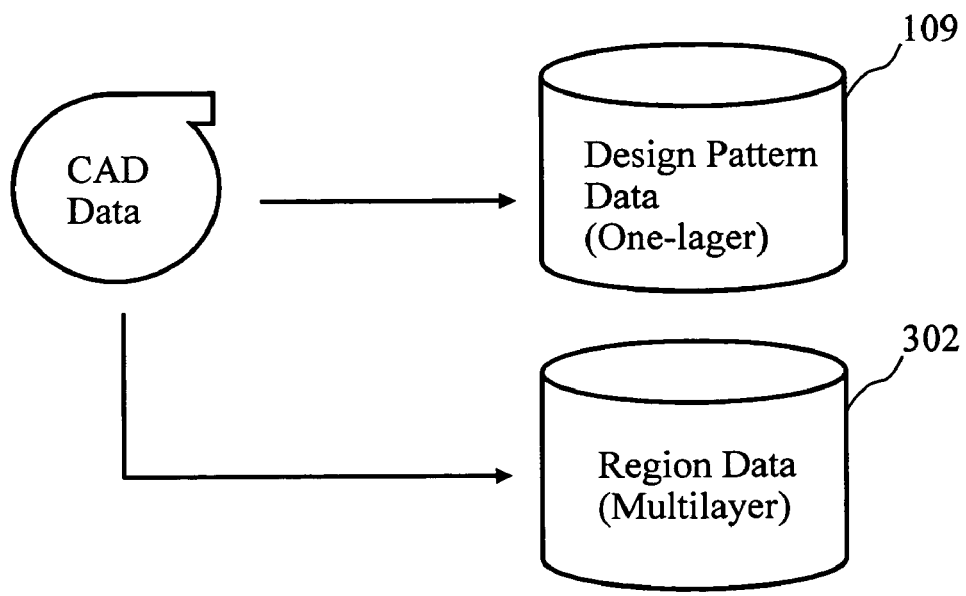
FIG. 5 is a pictorial representation for explanation of design pattern data and region data.

FIG. 5 is a pictorial representation for explanation of the design pattern data and region data. In the die-to-database inspection, input design pattern data (graphics data) which is obtained by conversion of pattern-designed CAD data to have a device input format that was input by photolithography equipment when drawing a pattern on the mask. Then, store the input data in the magnetic disk device 109, which is an example of the storage device (storage unit). In the design pattern data, basic and auxiliary patterns are represented as data in the same layer. In other words, both of the basic and auxiliary patterns are represented as graphics data together with layout coordinates thereof. On the other hand, extract region data from the CAD data in a way pursuant to the level of importance, thereby to create region data. Although the region data is not converted to have the device input format and thus is inconsistent in format with the design pattern data, any extra cares are not taken. The design pattern data is input to the workpiece inspection apparatus 100 and then stored in the magnetic disk device 109. The region data is input to the assistance device 300 and then stored in the magnetic disk device 302 in a way as will be described later.

At the pattern expansion step S146, the expander circuit 111 reads the design pattern data out of the magnetic disk device 109 via the control computer 110. Then, convert the readout design pattern data for use as the design graphic data of the photomask 101, i.e., workpiece, into two-value or multiple-value pixel bit data (design image data), which will be sent forth to the reference circuit 112.

Figure 6:
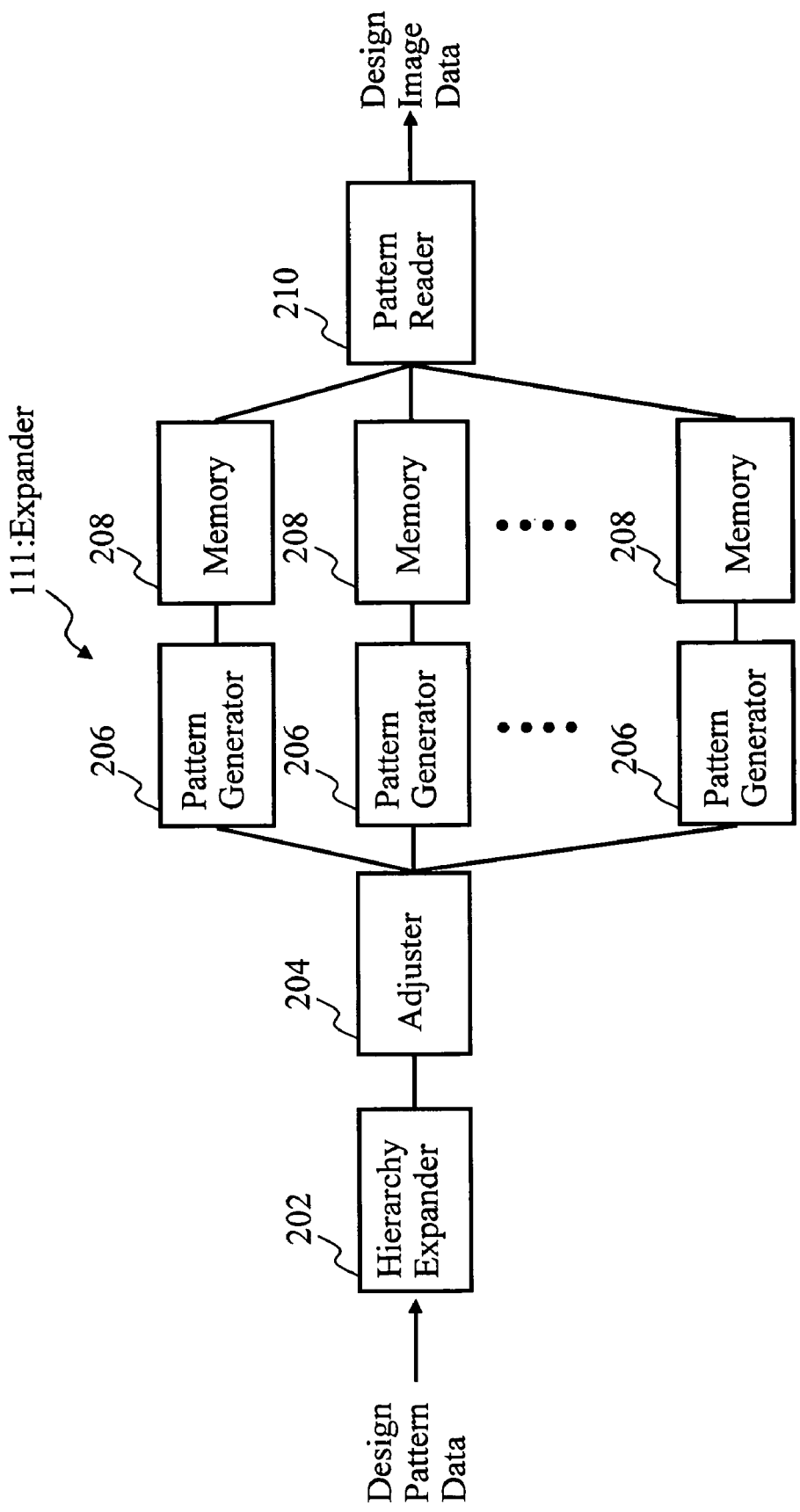
FIG. 6 depicts an exemplary configuration of an expansion circuit.

FIG. 6 is a diagram showing an exemplary configuration of the expander circuit 111. In FIG. 6, the expander 111 includes a hierarchical structure expansion circuit 202, an adjustment circuit 204, pattern generation circuits 206, pattern memories 208 and a pattern readout circuit 210. The pattern generators 206 and memories 208 are arranged so that a plurality of stages of pattern-generator/memory pairs are disposed.

Note here that the graphic forms as contained in the design pattern data are with rectangles and triangles as the basic figures; for example, graphics data defining each pattern's shape, size, position and others are stored in the form of information items such as coordinates (x,y) at graphics standard positions, side edge lengths, graphic codes for use as identifiers which distinguish graphic species such as rectangles and triangles or else.

Upon input of such design pattern data for use as the graphics data to the expander circuit 111, the hierarchical structure expansion circuit 202 expands the input data up to data items in units of graphic forms, and then interprets graphic sizes and graphic codes indicative of graphic shapes of the graphics data. Then, the pattern generator circuit 206 operates to expand two-value or multivalue design image data as a pattern to be disposed within a cell(s) with a grid of a specified quantization size being as a unit. The expanded design image data is temporarily stored in the pattern memory 208. In other words, the pattern generator 206, which exemplifies an occupation ratio computing unit, reads the design pattern data and computes the occupation ratio of a graphic form in the design pattern data per each cell, which is defined by virtual division or "dicing" of the test area with a dice of a prespecified size as a unit, and then outputs resultant n-bit occupation ratio data to the pattern memory 208. A preferable example is that one dice is set as a single pixel. Assuming that one pixel is designed to have a resolution of 1/28 (=1/256), compute an occupation ratio within the pixel while assigning thereto small regions of 1/256 in a way corresponding to the region of a graphic as disposed in the pixel. Then, output the result to pattern memory 208 as 8-bit occupation ratio data, for example.

Here, in order to permit the multiple pattern generator circuits 206 to effectively perform parallel processing operations, the adjustment circuit 204 distributes input data to each pattern generator 206. Then, the pattern reader 210 reads the occupation ratio data being stored in the pattern memory 208. At pattern reader 210, when the occupation ratio data within the same pixel are present, add them together for readout, whereby a graphic occupation ratio (gray-scale value) within each pixel is identifiable.

At the filtering step S148, the reference circuit 112 receives the design image data, i.e., the graphic pixel bit data as sent thereto, and then applies adequate filtering to the data.

Figure 7:
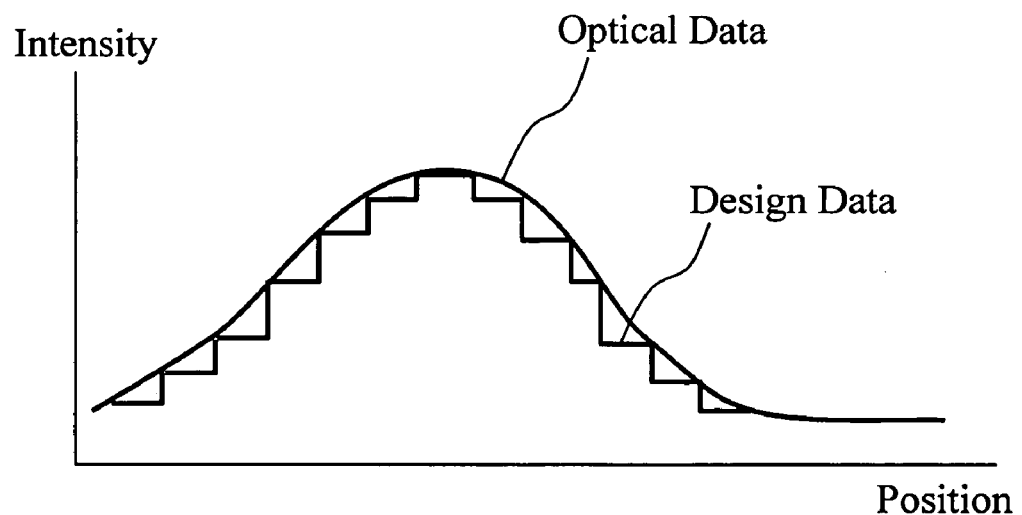
FIG. 7 is a graph for explanation of filtering.

FIG. 7 is a graph for explaining the filtering process.

The measured data as to the optical image obtained from the sensor circuit 106 is applied filtering due to resolution characteristics of the magnifying optics 104 and/or aperture effects of the PD array 105—in other words, in an analog state with continuous variability. Accordingly, by applying the filtering also to the design image data, i.e., the pixel bit data on the design side with the image intensity (variable-density or shade value) being of digital values, it is possible to match the design image data with the measured data. In this way, the reference data representing a reference image for comparison to the optical image is prepared and then sent to the data distribution processor circuit 140.

At the data distribution processing step S150, the data distribution processor circuit 140 transfers the reference data to the comparator circuit 108 while at the same time establishing synchronization between the measured data and the test region to be compared.

At the storage step S152, let the reference data be sequentially sent to and temporarily stored in the reference data memory 174 in the comparator 108.

Here, mere comparison of the measured data to the reference data would result in generation of false or "pseudo" defects as stated supra. In the embodiment 1 the assistance device 300 shown in FIG. 1 creates regional image data for input to the comparator circuit 108. As previously stated, with the miniaturization of circuit patterns in recent years, it becomes more difficult to achieve the matching between the reference data and the measured data to a degree that precludes occurrence of any appreciable pseudo-defects. This is mainly due to difficulties in uniformly drawing a pattern over the entire workpiece surface and/or the formation of a locally complex pattern(s). To avoid this risk, the illustrative embodiment 1 is arranged to include the assistance device 300 separately from the workpiece inspection apparatus 100 for generating regional image data and also employ a technique for using such data to render a decision threshold for comparison inspection variable, thereby providing a comparison processing system capable of restraining occurrence of pseudo-defects.

At the region data input step S102, the assistance device 300 inputs region data from an input device (not shown). An example of the input device used is the external I/F 312. Other examples include, but not limited to, magnetic tape devices and FD drive units.

At the storage step S104, let the region data be stored in the magnetic disk device 302, which is an example of the storage device (storage unit).

In the data conversion step S106, the data conversion processor circuit 304 reads the region data out of the magnetic disk device 302 and converts the read data to two-value or multivalue pixel pit data (regional image data), which will be sent to the data memory 306.

Figure 8:
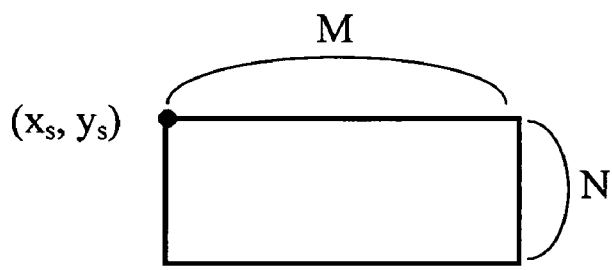
FIG. 8 is a diagram showing an example of the region data.

FIG. 8 is a diagram showing one example of the region data.

A region or "zone" as contained in the region data is with rectangles as its basic figure. For example, there is stored therein graphic data defining the size and position or else of a graphic form that represents each region by the information as to the coordinates (x,y) at graphic's standard positions and side lengths.

Figure 9:
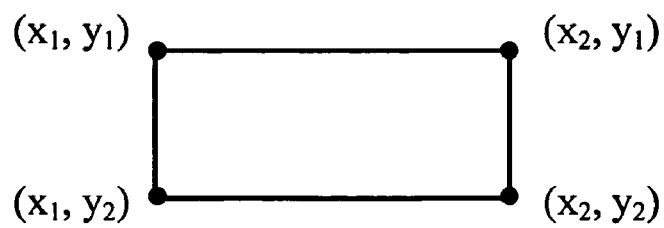
FIG. 9 is a diagram showing another example of the region data.

FIG. 9 is a diagram showing another example of the region data.

Also preferably, the region included in the region data is such that the coordinates (x,y) of four apexes of a rectangle are used to define the size and position of a graphic form which indicates each region.

Figure 10:
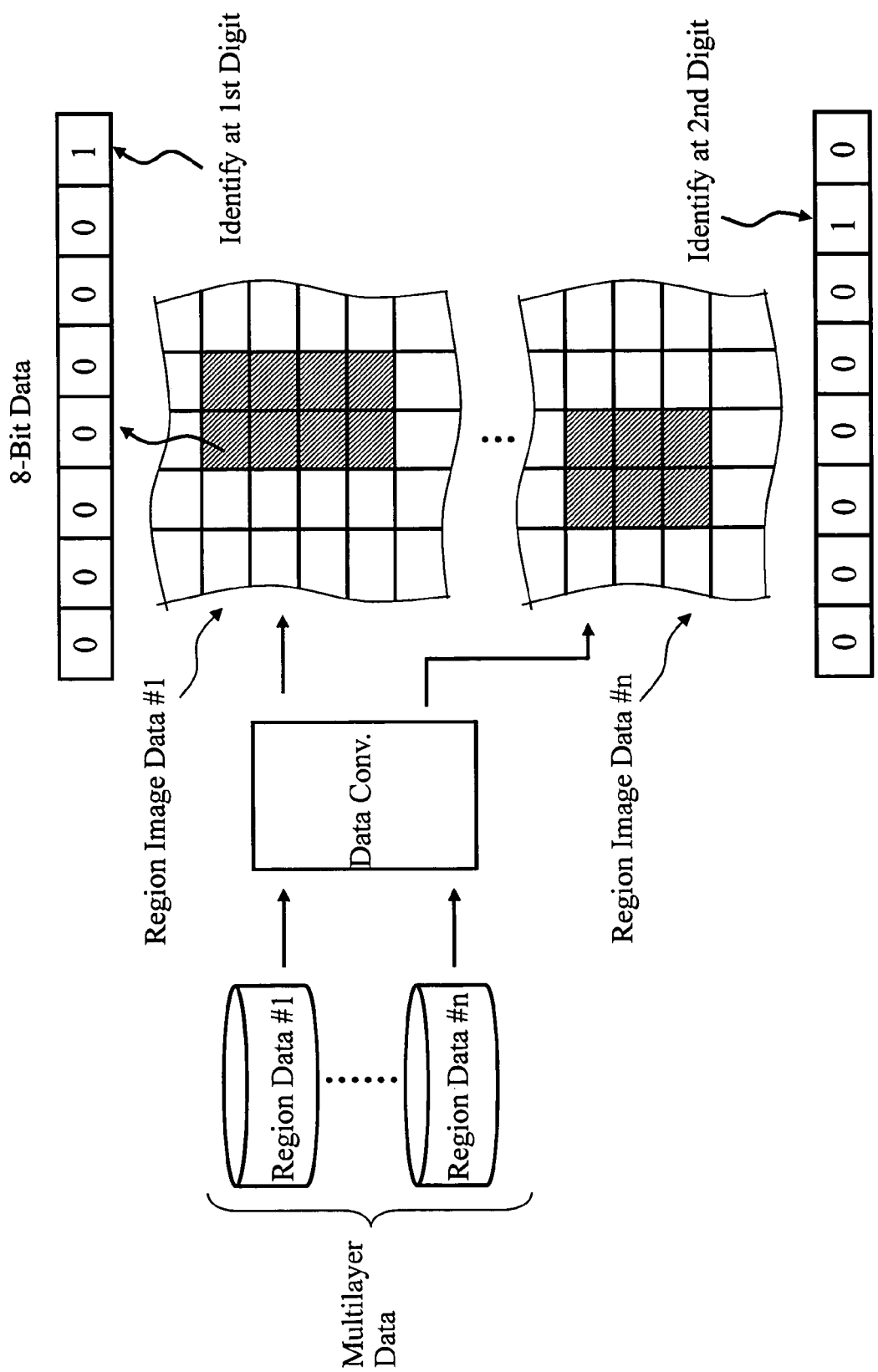
FIG. 10 is a diagram for explanation of the conversion of from the region data to regional image data.

FIG. 10 is a diagram for explanation of the conversion of from the region data to regional image data.

The region data may be such that a plurality of regions are defined (converted to multilayer data) respectively. In FIG. 10, suppose for example that region data 1, region data 2, . . . , region data n are included. Such region data is/are converted by the data converter 304 to pixel bit data. In FIG. 10, those pixels hatched are the region of interest. In case 8-bit data conversion is done on a per-pixel basis, the digit number flagged with a logic "1" is changed in a way which follows: at pixels corresponding to the region in the region data 1, a "1" is flagged at the first digit thereof; at pixels corresponding to the region in the region data n, "1" is flagged at its second digit. This is preferable because of its region identifiability.

At the data distribution processing step S108, let the data distribution processor circuit(s) 308 send the regional image data from the external I/F 312 to the comparator circuit 108 while forcing a test region to be synchronized with the measured data and reference data in a way of matching with an inspection speed of the workpiece inspection apparatus 100. By allowing a plurality of data distribution processors 308 to perform parallel processing, it is possible to retain the data communication rate for synchronization of the test region with the measured data and reference data. Such processing may be done by a single stage of data distribution processor 308 as far as the test region is synchronizable with the measured data and reference data. Additionally the multiple data distribution processors 308 are controlled by the distribution control circuit 310. Optionally the transfer unit may be set to a band-shaped region as divided from an entire mask region, or to further fine ones.

At the regional image data input step S110, let the regional image data be input to comparator 108 via external I/F 142. The workpiece inspection apparatus 100 and assistance device 300 are communicably linked together by a local area network (LAN) as an example. In particular, in order to increase the communication rate, it is preferable to employ a gigabit LAN using an optical cable or else.

At the storing step S114, let the input regional image data be sequentially sent via the bus 120 to the regional image memory 172 in the comparator circuit 108 and then temporarily stored therein.

At the comparison step S160, the comparison processor circuit 178 in the comparator circuit 108 accepts the optical image data for use as the measured data of a test pattern generated by the sensor circuit 106 based on the optical image obtained from the workpiece, i.e., photomask 101, the reference image data for use as design image data generated at the expander circuit 111 and reference circuit 112, and the regional image data as input from the assistance device 300. Then, use the regional image data as decision threshold modifying data for updating a decision threshold to change the decision threshold (inspection sensitivity) based on the regional image data, upon comparison of the optical image data and reference image data. Next, perform comparison in accordance with a predetermined algorithm to thereby determine or "judge" whether defects are present or absent. Providing a plurality of stages of comparison processors 178 for execution of parallel processing is preferable in order to shorten the inspection time. It is also preferable to design the comparison processor 178 to have a plurality of built-in data processing means.

Note here that the measured data may be compared to the design image data while varying the decision threshold (inspection sensitivity) based on the regional image data at regular time intervals. Alternatively, upon detection of a defective portion (no good or "NG" part) during comparison with the design image data, an inspection threshold (test sensitivity) that becomes the decision criteria is altered based on the regional image data for redoing the comparison between the measured data and design image data. This is more preferable when taking account of a time taken for the comparison process. In other words, it is permissible that in case the comparison of the measured data for use as the optical image data and the design image data in the comparator circuit 108 results in a difference therebetween exceeding a predefined threshold, the regional image data is used to modify the decision threshold (test sensitivity) and then perform again the comparison of the measured data and design image data.

With such arrangement, the regional image data is transferred on a real-time basis to the comparator circuit 108 in the workpiece inspection apparatus 100, which comparator is capable of performing high sensitive defect judgment using the regional image data on a real time basis while varying the comparative decision threshold of a region to be compared. Hence, certain regions that must be subjected to strict defect inspection are inspected using a strict decision threshold while allowing relatively immaterial regions to undergo loosened defect check at a "mild" decision threshold. This makes it possible to prevent frequent occurrence of pseudo-defects.

Furthermore, by providing the assistance device 300 which directly inputs from the outside the regional image data in synchronism with the defect detection processing within the workpiece inspection apparatus 100 in a way independent of the inspection apparatus 100, it is possible to retain the affinity and extendability relative to the apparatus 100 while avoiding risks as to excessive complexity and cost increase plus elongated development periods of the inspection apparatus occurring due to improvements in existing workpiece inspection apparatus.

An explanation will now be given of some patterns in which pseudo-defects are readily occurrable in the case of comparison inspection of the measured data to the reference data.

Figure 11:
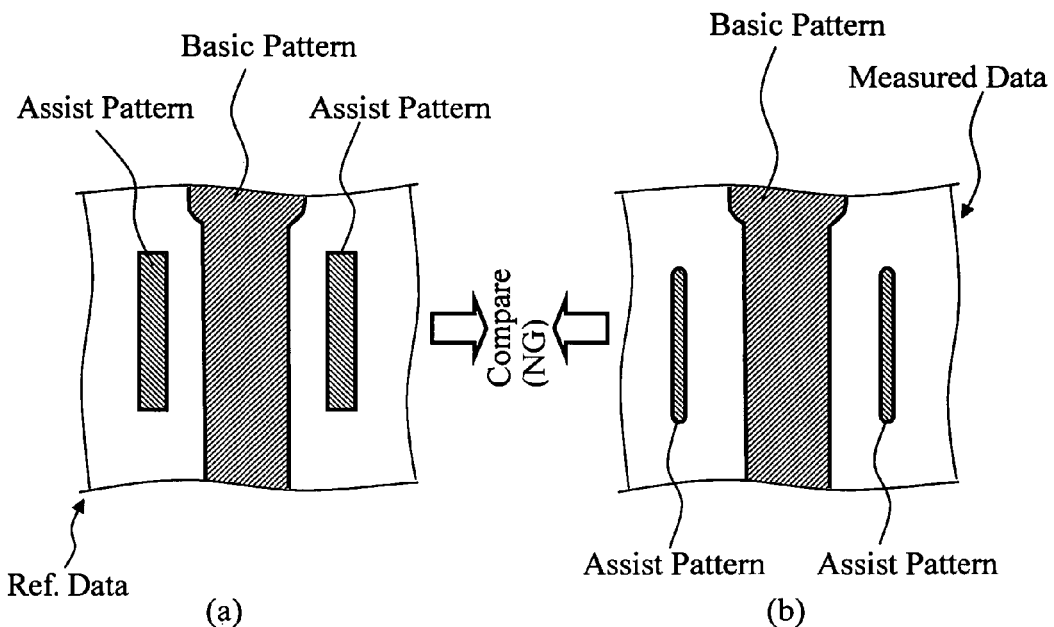
FIG. 11 shows exemplary OPC pattern-disposed reference data and measurement data.

FIG. 11 is a diagram showing an exemplary combination of measured data and assist pattern-disposed reference data.

In FIG. 11, a line pattern is formed as the basic pattern. Optical proximity correction (OPC) is used in some cases at an edge portion of such basic pattern, which is formed so that the linewidth is increased or "ballooned" outwardly. A pair of assist patterns reside on the opposite sides of the basic pattern, wherein the former is less in linewidth than the latter.

When comparing the measured data shown in part "b" of FIG. 11 to the OPC pattern-disposed design image data (reference data) as created from the design pattern data, the assist patterns become smaller unintentionally. Hence, mere execution of the comparison between the measured data and reference data with no extra processing applied thereto can sometimes result in judgment of a defect (NG).

As apparent from the foregoing, the assist patterns are impermissibly narrower in linewidth or less in length than those patterns that are mainly used in the workpiece of interest as shown in FIG. 11. In addition, more than one of the patterns on the workpiece which are actually drawn from this design pattern data often fails to be accurately formed as shown in part b of FIG. 11. If this is simply inspected using a similar comparison threshold to that of other patterns, then the inspection apparatus can erroneously recognize it as a defect in some cases.

However, whether this pattern is completed accurately in size is not so important in many events, and judging it as a defect results in occurrence of an increased number of pseudo-defects on the entire workpiece surface. This in turn causes the number of the user's test result reviewing activities to go beyond the limit. To avoid this, specific region setup is done in a way which follows.

Figure 12:
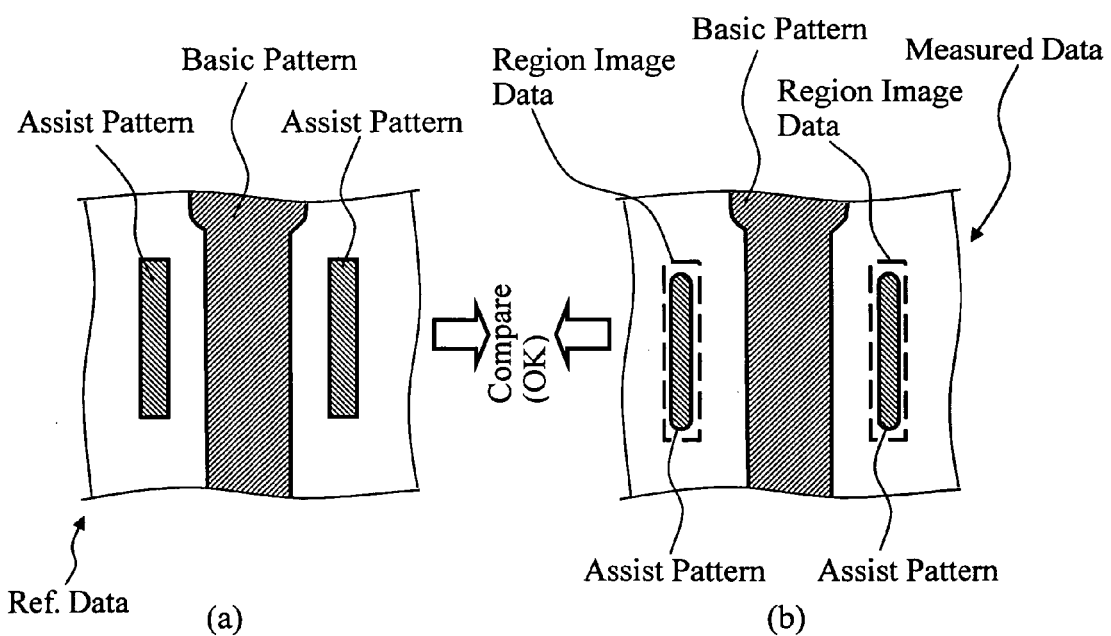
FIG. 12 is a diagram for explanation of a region indicated by the regional image data.

FIG. 12 is a diagram for explanation of a region as indicated by the regional image data.

Prepare region data for use as the "source" of regional image data indicative of an assist pattern-adjacent region, which is not necessarily inspected with strict test sensitivity as shown at part b of FIG. 12. Then, convert the region data to regional image data for input to the comparator circuit 108. This permits the comparator 108 to automatically loosen the comparison threshold in vicinity to this region. Thus it becomes possible to preclude misjudgment of those pattern portions being incorrectly regarded as defects—namely, pseudo-defects—in the prior art. Desirably the region data may be designed to represent a region that has slightly larger in size than portions to be designated (here, assist pattern segments) in view of position deviation errors. For example, it is recommendable to let it be a region with its size being enlarged by a degree equivalent to a single pixel as a whole.

Figure 13:
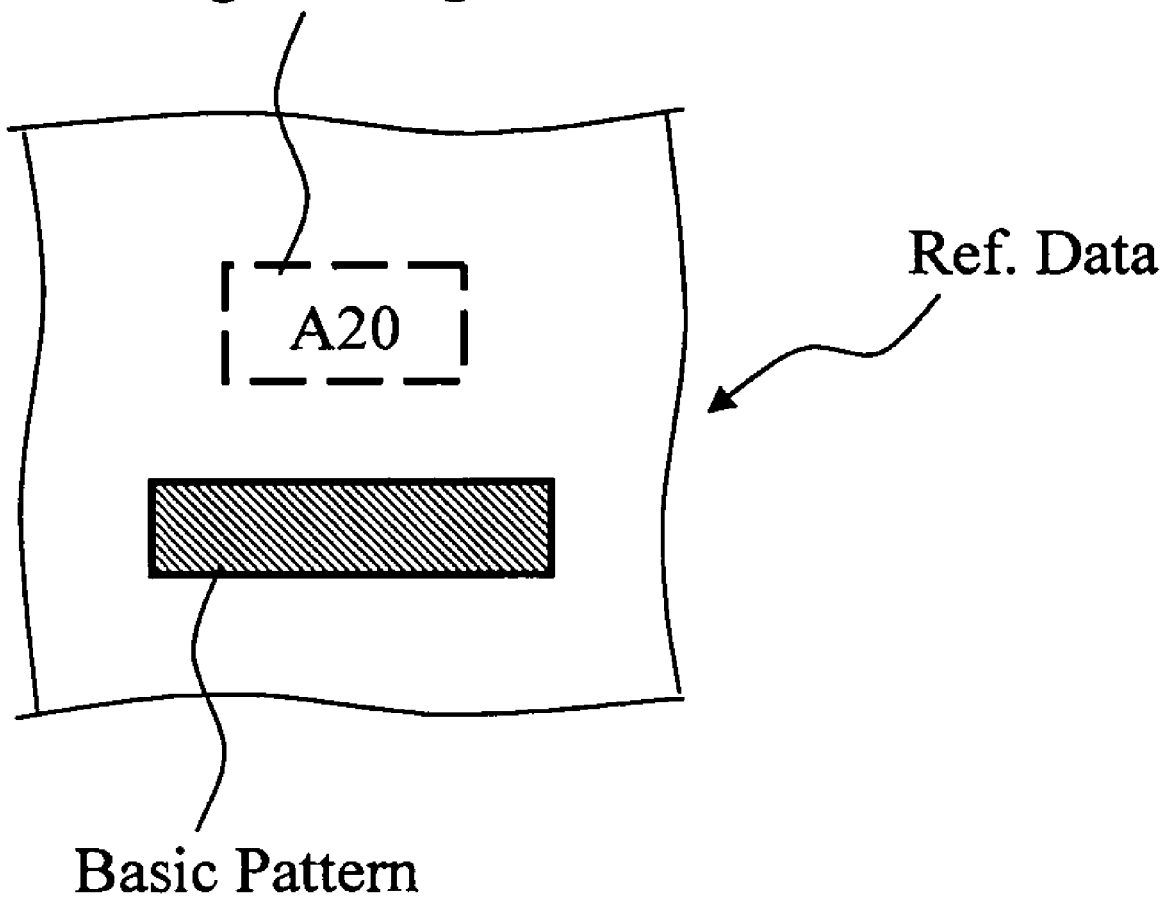
FIG. 13 shows another example for explanation of the region indicated by the regional image data.

FIG. 13 is a diagram showing another example for explanation of the region denoted by the regional image data. An indication "A20" shown in FIG. 13 is a string of characters as recited in the surface of a workpiece, such as a mask or else. Usually this character part need not be inspected at high sensitivity. Thus it is also preferable to prepare region data for use as the source of regional image data indicating a region(s) adjacent to such character part without the need to tighten the inspection sensitivity and then convert the region data to regional image data for input to the comparator circuit 108. The same goes with dummy patterns. Adversely, contact patterns or equivalents thereto are such that positional deviation and deformation are very likely to cause electrical disconnection and shorting of pattern circuitry. In view of this, it is also preferable to provide region data for use as the source of the regional image data indicative of those regions residing near such portion with the test sensitivity tightened, and then convert the region data to regional image data for input to the comparator 108.

It is possible to reduce pseudo or quasi-defects by preparing the region data and then using the regional image data to be created from the region data to compare the measured data with the design image data as formed from the design pattern data in the way stated above.

Embodiment 2

Although the embodiment 1 explained above is specifically directed to the case of the die-to-database inspection for comparing the measurement data to reference data based on the design image data as created from the design pattern data, the regional image data is also preferably applicable to the "die to die" inspection, which compares together optical image data items obtainable by the image-sensing of identical patterns at different locations on the same mask.

Figure 14:
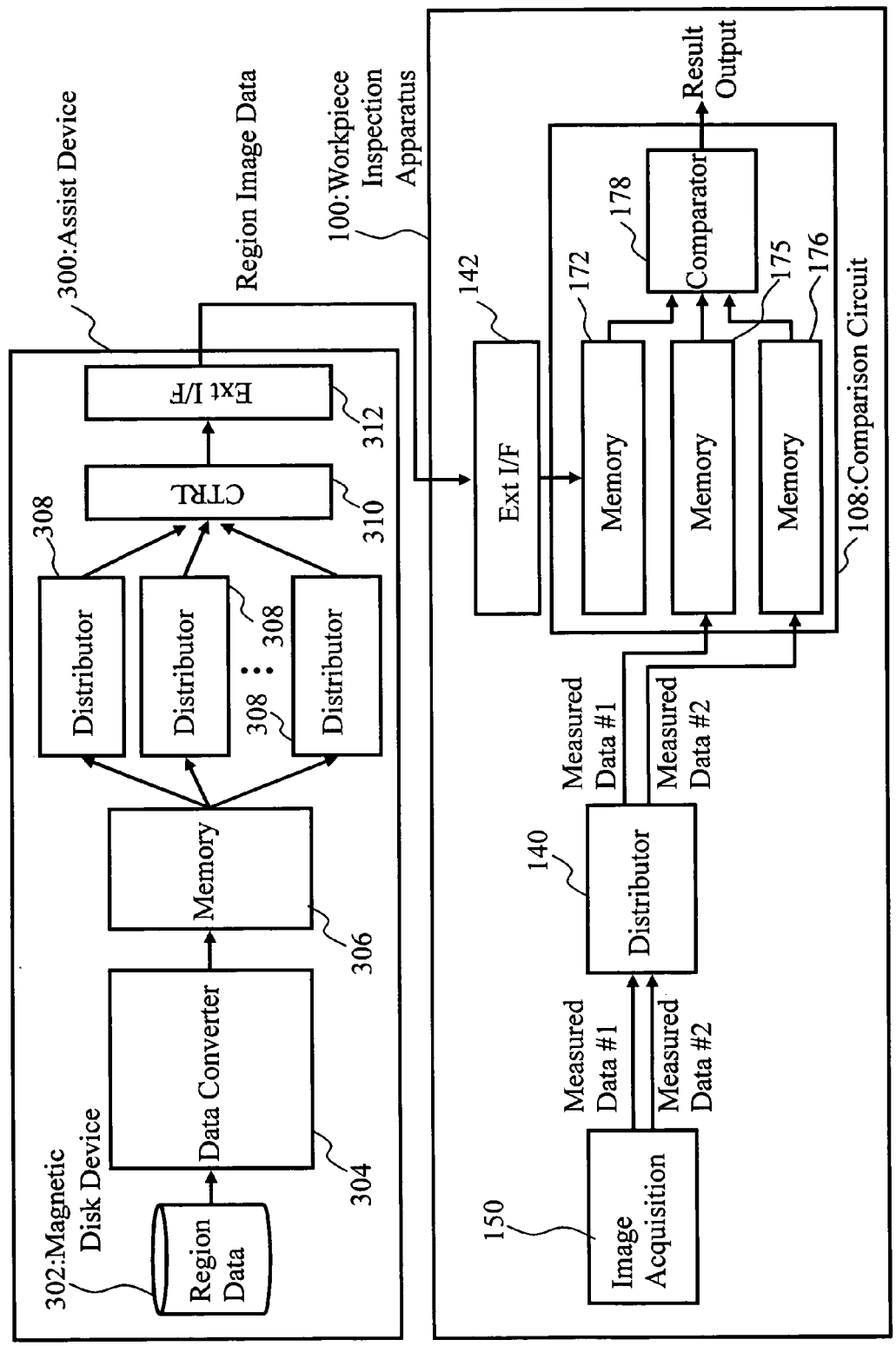
FIG. 14 is a block diagram showing a major configuration of a workpiece inspection apparatus and an assistive device in an embodiment 2.

FIG. 14 is a block diagram showing a major configuration of a workpiece inspection apparatus and an assistance device in an embodiment 2. In FIG. 14, the assistance device 300 of workpiece inspection apparatus 100 is similar to that of the embodiment 1 stated supra, so its explanation is eliminated herein. The workpiece inspection apparatus 100 includes an optical image acquisition unit 150, data distribution processor circuit 140, external interface (I/F) 142, and comparison circuit 108. The comparator circuit 108 has a regional image memory 172, measured data memories 175-176, and comparison processing circuit 178. In FIG. 14, those other than necessary constituent components for explanation of this embodiment 2 are omitted. Obviously the workpiece inspection apparatus 100 and assistance device 300 are usually designed to include other arrangements required for reduction to practice.

In FIG. 14, the optical image acquisition unit 150 acquires a plurality of measurement data (optical image data) resulted from image pickup of identical patterns at different locations on the same mask. Here, it acquires measured data No. 1 and measured data No. 2. Then, these data items are sent by the data distribution processor circuit 140 to the comparator circuit 108 while letting a test region be synchronized therewith. In the comparator 108, the measured data #1 and measured data #2 are sequentially sent to and temporarily stored in the measured data memories 175-176, respectively. On the other hand, receive regional image data as input from the assistance device 300 in a similar way to that of the embodiment 1; then, sequentially send the data to the regional image memory 172 for temporary storage therein. Next, a comparison process is done by the comparison processor circuit 178 in the comparator 108. At this step, the comparison processor 178 fetches the measured data #1 and #2 of a pattern under inspection as generated by the sensor circuit 106 based on a transmitted image obtainable from a workpiece, i.e., photomask 101, along with the regional image data as input from the assistance device 300, and modifies a decision threshold (inspection sensitivity) based on the regional image data, and then compares together optical image data (in other words, measured data and reference data while regarding one of the optical image data as reference data) in accordance with a prespecified algorithm to thereby determine whether defects are present or absent.

In the die-to-die inspection, fluctuations of light or else can sometimes give rise to deviation in pattern shapes of the measured data. In particular, when compared to basic patterns such as assist patterns, linewidth-reduced or "slim" patterns are readily affectable by such fluctuations. Accordingly, by changing or updating the decision threshold (test sensitivity) based on the regional image data, it is possible to reduce pseudo-defects otherwise occurring due to the influence of such fluctuations.

Embodiment 3

While in each of the above-stated embodiments the assistance device 300 is designed to convert the region data to pixel bit data for output to the workpiece inspection apparatus 100, an embodiment 3 is arranged to provide specific data being less in size than the pixel bit data for output to the inspection apparatus 100 in a way as will be set forth below.

Figure 15:
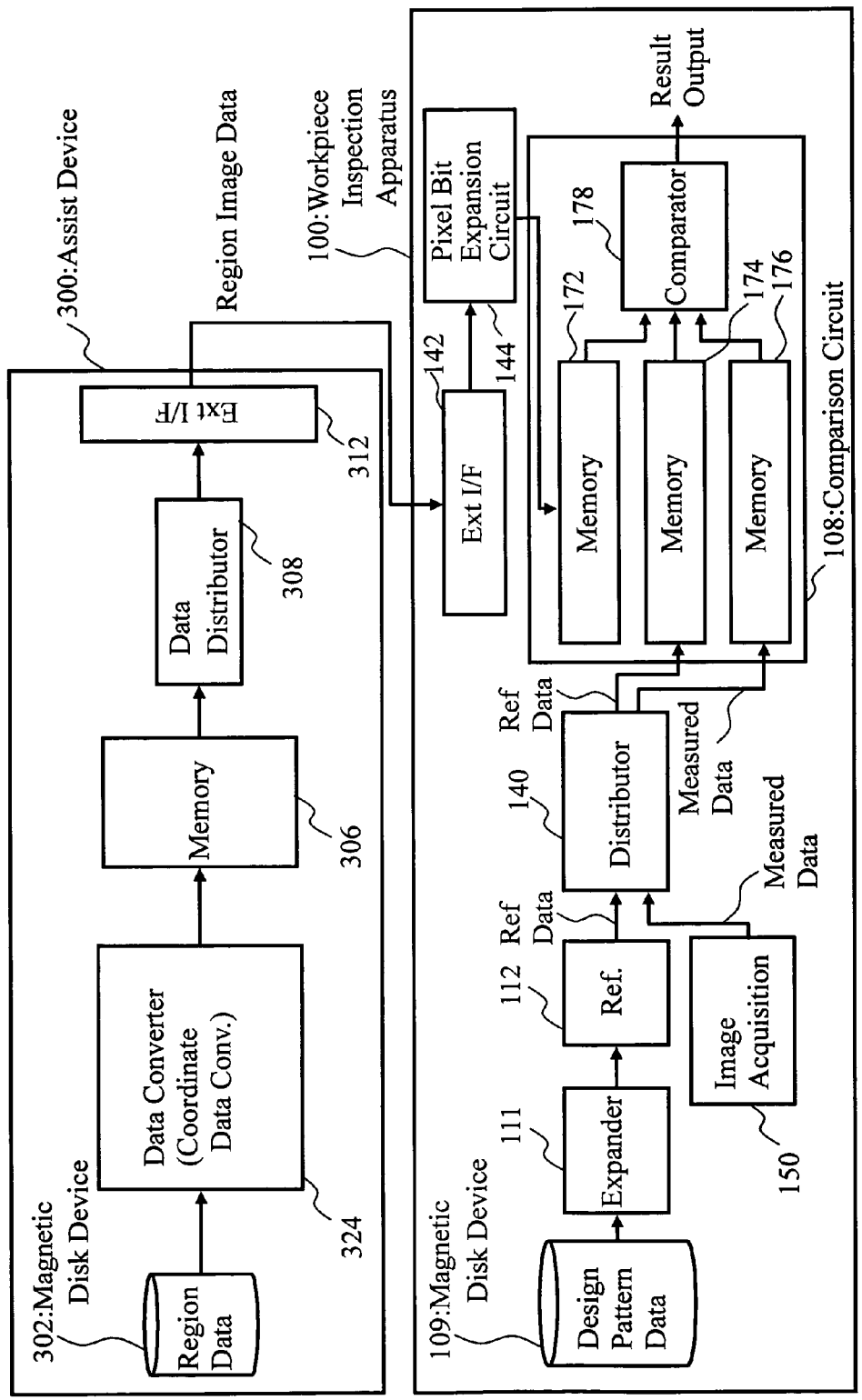
FIG. 15 is a block diagram showing a major configuration of a workpiece inspection apparatus and assistance device in an embodiment 3.

FIG. 15 is a block diagram showing a major configuration of a workpiece inspection apparatus and its assistance device in the embodiment 3.

In FIG. 15, the assistance device 300 includes a magnetic disk device 302, a data conversion processing circuit 324 which is an example of the regional image data conversion unit as claimed, a data memory 306, a data distribution processing circuit 308 that is an example of the data distribution processing unit, and an external I/F 312. This arrangement is different from that of FIG. 1 in function of the data conversion processor 324. Additionally the data distribution processor 308 consists of a one stage of circuitry. Owing to the use of one stage, it is possible to omit the distribution control circuit 310. As for the workpiece inspection apparatus 100, this includes a magnetic disk device 109, expander circuit 111, reference circuit 112, optical image acquisition unit 150, data distribution processor circuit 140, external I/F 142, pixel bit expansion circuit 144, and comparison circuit 108. The comparator 108 has a regional image memory 172, reference data memory 174, measured data memory 176, and comparison processor circuit 178. This configuration is similar to that of FIG. 1 with the pixel bit expander 144 being added thereto. In FIG. 15, those other than the necessary components for explanation of this embodiment 2 are omitted. Obviously the workpiece inspection apparatus 100 and assistance device 300 are generally designed to come with other components required for practical implementation.

Figure 16:
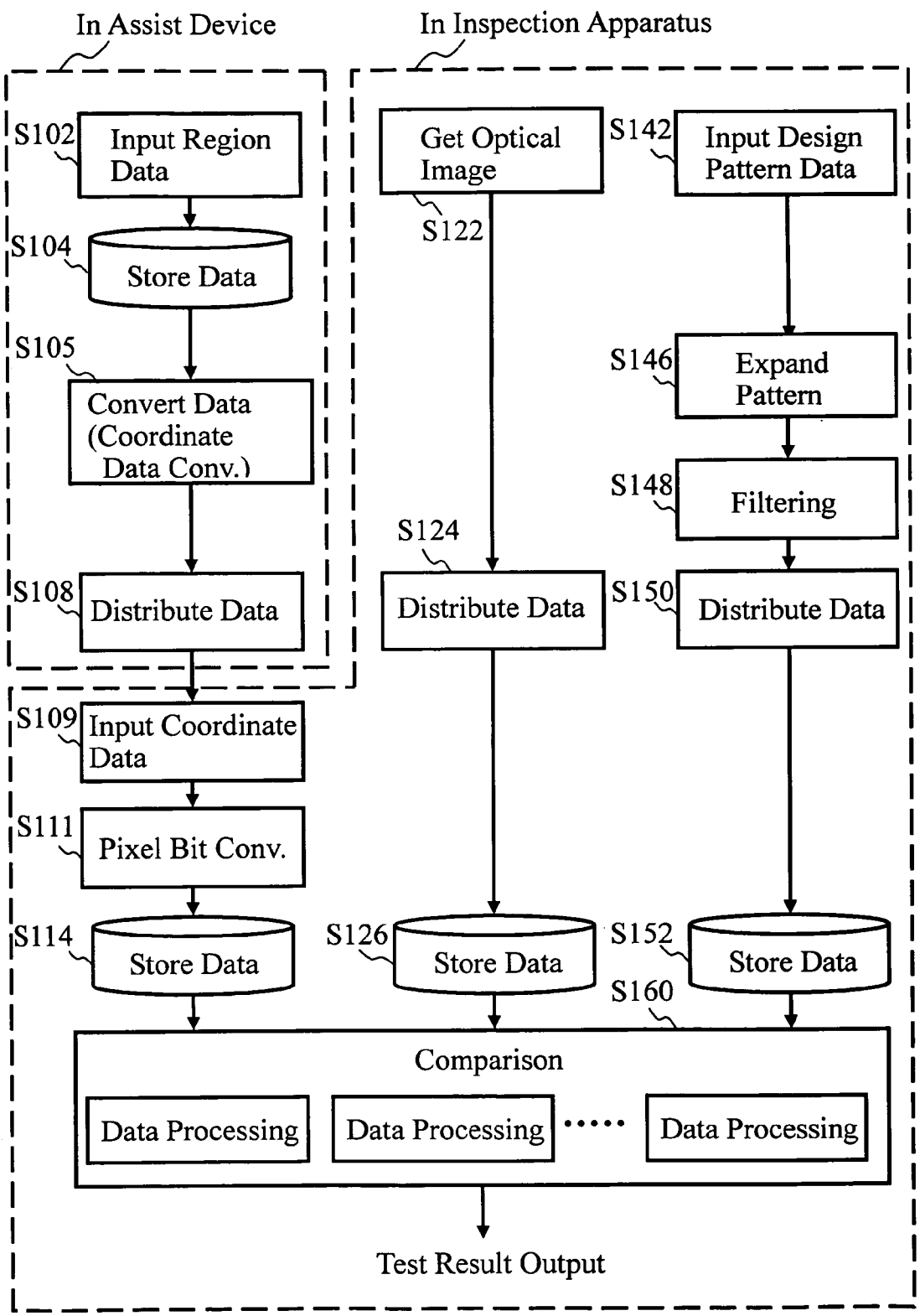
FIG. 16 is a flowchart showing some major process steps of a workpiece inspection method for use in the inspection apparatus and assistance device in the embodiment 3.

FIG. 16 is a flowchart showing some major process steps of a workpiece inspection method for use in the workpiece inspection apparatus and assistance device in the embodiment 3.

In FIG. 16, the workpiece inspection method includes a series of processes as executed in the assistance device 300, including a region data input step (S102), storing step (S104), data conversion step (S105), and data distribution processing step (S108). The inspection method also includes a series of processes to be performed in the inspection apparatus 100, including a coordinate data input step (S109), pixel bit conversion step (S111), storage step (S114), optical image acquisition step (S122), data distribution processing step (S124), storage step (S126), design pattern data input step (S142), pattern expansion step (S146), filtering step (S148), data distribution processing step (S150), storage step (S152), and comparison step (S160).

The region data input step (S102) and storage step (S104) in FIG. 16 are similar to those of the embodiment 1, so explanations thereof will be eliminated herein. At the data conversion step S105, the data converter circuit 324 reads region data out of the magnetic disk device 302 and then converts the read data to coordinate data (one example of the second region data) in compliance with prescribed rules. The coordinate data will be sent to the data memory 306.

As previously stated, a region contained in the region data is with rectangles as its basic figure as shown in FIG. 8 or 9. For example, graphic data defining the size and position or else of each region are stored in the form of the information such as coordinates (x,y) and side length at standard positions of the figure.

Figure 17:
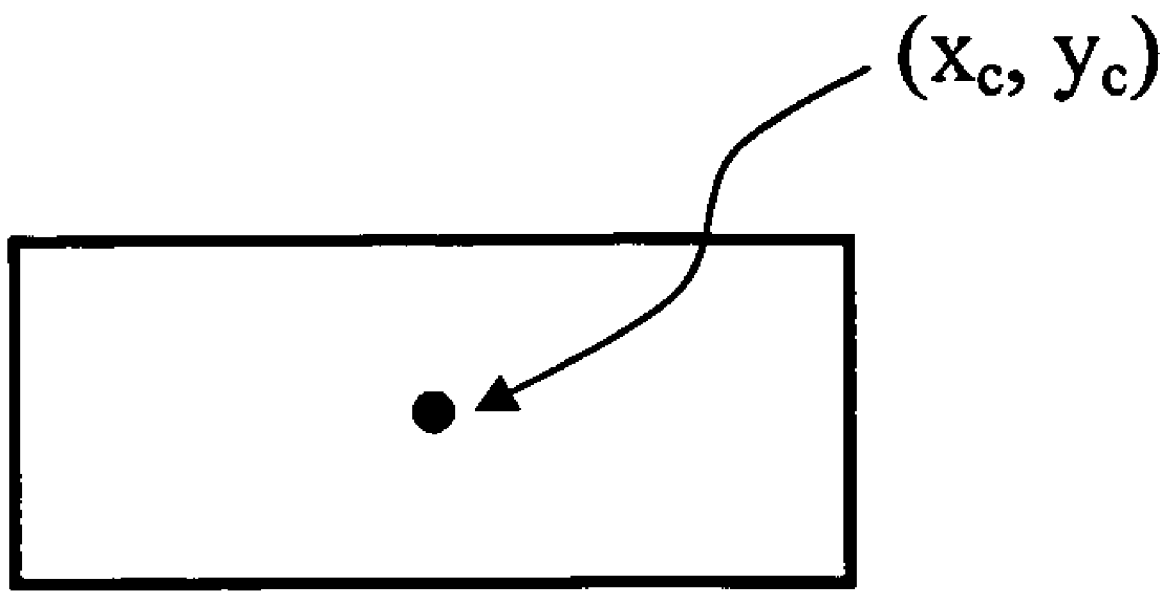
FIG. 17 shows an example of coordinate data.

FIG. 17 shows an example of the coordinate data. In FIG. 17, the region included in the region data is defined by centroid position coordinates $(x_c, y_c)$ only, as an example. Side lengths or the like are predefined in a way communicable with the workpiece inspection apparatus 100 to enable recognition of the region by such centroid position coordinates $(x_c, y_c)$, whereby it becomes possible to output the required data to inspection apparatus 100 in the form of the data being less in size than the pixel bit data in the embodiment 1. Lessening the data size makes it possible to increase the data communication speed. Alternatively it is possible to downsize the data distributor circuit 308.

At the data distribution step S108, the data distributor 308 sends the coordinate data from the external I/F 312 to the comparator circuit 108 while letting a test region be synchronized with the measured data and reference data in a way matched with the inspection speed of the workpiece inspection apparatus 100.

At the coordinate data input step S109, the coordinate data is input to the comparator circuit 108 via the external I/F 142. For example, LAN is used to connect between the inspection apparatus 100 and assistance device 300. In particular, in order to speed up communications, it is preferable to employ gigabit LAN using an optical cable or else, as stated previously.

At pixel bit conversion step S111, the pixel bit expander circuit 144 reads the coordinate data as input to the external I/F 142 and then converts the read data into regional image data of pixel bit data, which is sent to the data memory 306.

Regarding the storage step (S114), optical image acquisition step (S122), data distribution step (S124), storage step (S126), design pattern data input step (S142), pattern expansion step (S146), filtering step (S148), data distribution step (S150), storage step (S152) and comparison step (S160), this embodiment is similar to the embodiment 1, so explanations thereof are eliminated herein.

By representing a one region by two-dimensional 2D) coordinates in the way stated above, it is possible to reduce the data size to an extent that is the half of or less than the regional image data of pixel bit data. This in turn makes it possible to increase the communication rate, thereby enabling prevention of its delay relative to the processing speed of the workpiece inspection apparatus 100.

In the inspection apparatus 100, patterns are processed as image information. Thus a need is felt to expand this information into pixel bits. This expansion to pixel bits may be performed in advance by a conversion processing means as in each of the above-stated embodiments. Alternatively the expansion may be done within the inspection apparatus 100 on a real-time basis as in this embodiment.

It is also preferable to apply this embodiment to the die-to-die inspection shown in the embodiment 2.

Embodiment 4

While in the embodiment 3 the pixel-bit expansion is internally performed in the workpiece inspection apparatus 100 in order to lessen the size of the data being output from the assistance device 300 to inspection apparatus 100, an embodiment 4 is arranged to lessen the size of the data for output to apparatus 100 while at the same time performing the pixel-bit expansion within the assistance device 300 in a way as will be set forth below.

Figure 18:
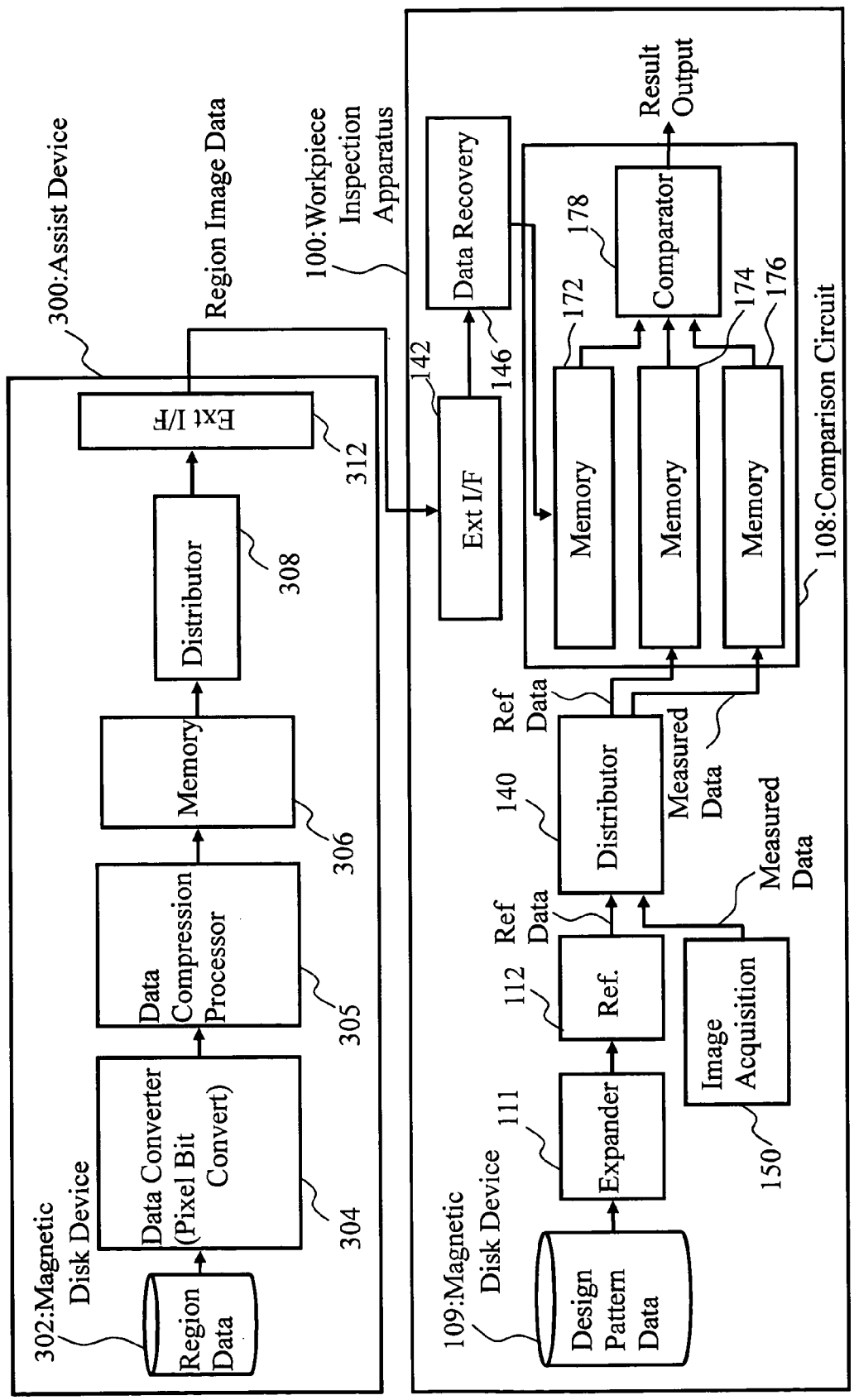
FIG. 18 is a block diagram showing a major configuration of a workpiece inspection apparatus and assistance device in an embodiment 4.

FIG. 18 is a block diagram showing a main configuration of a workpiece inspection apparatus and its assistance device in the embodiment 4.

In FIG. 18, the assistance device 300 includes a magnetic disk device 302, a data conversion processor circuit 304 which is one example of the regional image data conversion unit, a data compression processor circuit 305 which is an example of the compressed data conversion unit, a data memory 306, a data distribution processor circuit 308 that exemplifies the data distribution processing unit, and an external I/F 312. This configuration is different from that of FIG. 1 in that the data compressor circuit 305 is added. This data compressor 305 consists of a single stage of circuitry. Due to the one-stage design, it is possible to omit the distribution control circuit 310. On the other hand, the workpiece inspection apparatus 100 includes a magnetic disk device 109, expander circuit 111, reference circuit 112, optical image acquisition unit 150, data distribution processor circuit 140, external I/F 142, data recovery processing circuit 146, and comparator circuit 108. This comparator 108 has a regional image memory 172, reference data memory 174, measured data memory 176 and comparison processor circuit 178. This arrangement is similar to that of FIG. 1 with the data recovery processor 146 being added thereto. In FIG. 18, those other than necessary components for explanation of this embodiment 4 are omitted. Obviously the inspection apparatus 100 and assistant 300 usually include other arrangements required.

Figure 19:
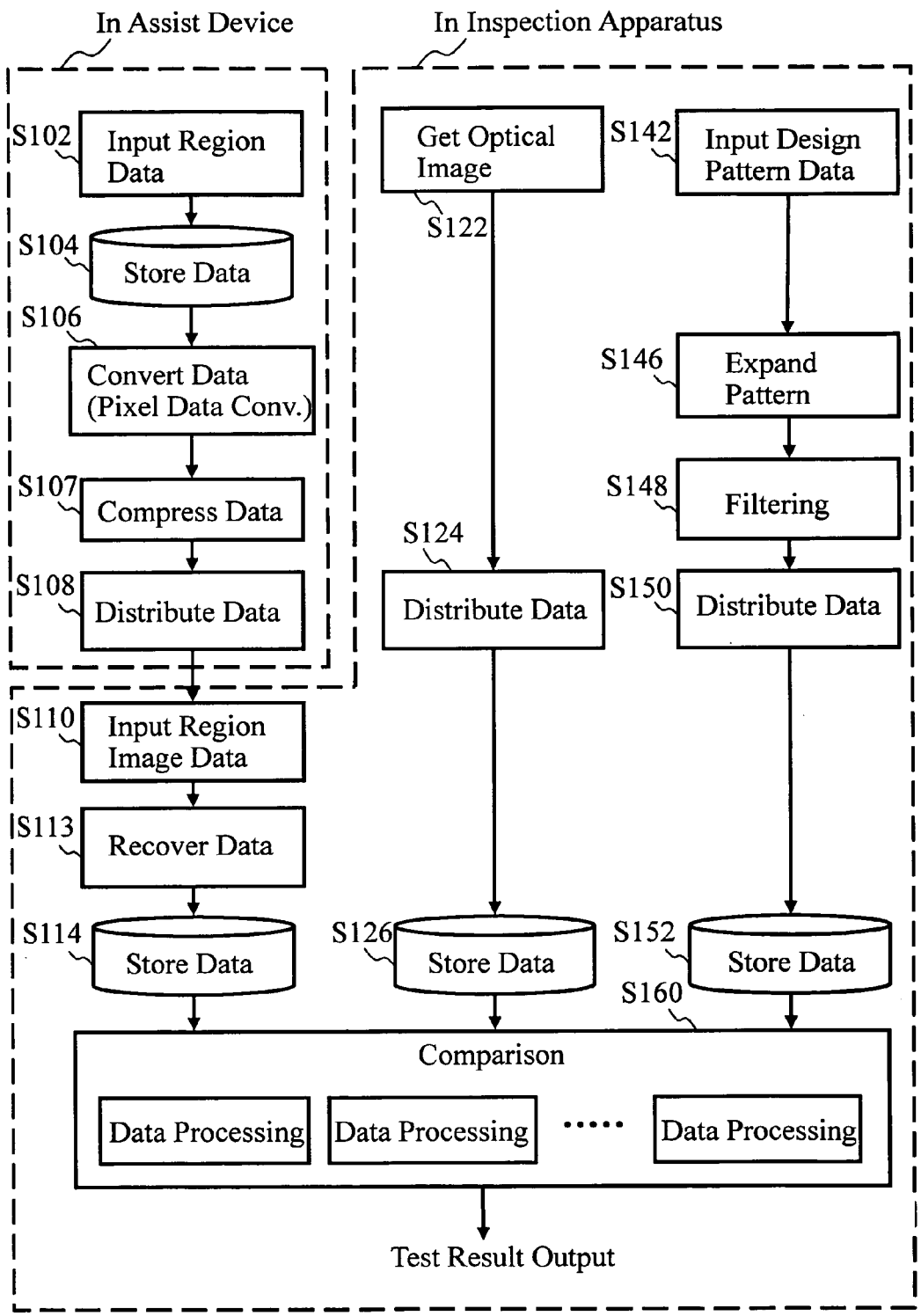
FIG. 19 is a flowchart showing major process steps of a workpiece inspection method for use in the inspection apparatus and assistance device in the embodiment 4.

FIG. 19 is a flowchart showing major process steps of a workpiece inspection method for use in the inspection apparatus 100 and assistant 300 in embodiment 4.

In FIG. 19, the inspection method includes a series of processes steps to be executed within the assistant 300, including a region data input step (S102), storage step (S104), data conversion step (S106), data compression step (S107) and data distribution processing step (S108). The method also includes a sequence of processes as executed in the inspection apparatus 100, including a regional image data input step (S110), data recovery step (S113), storage step (S114), optical image acquisition step (122), data distribution step (S124), storage step (S126), design pattern data input step (S142), pattern expansion step (S146), filtering step (S148), data distribution step (S150), storage step (S152) and comparison step (S160).

The region data input step (S102), storage step (S104) and data conversion step (S106) are similar to those of the embodiment 1. Thus, their explanations are omitted.

At the data compression step S107, the data compressor circuit 305 compresses the regional image data of pixel bit data. Then, send the compressed data to memory 306.

By compressing the regional image data, it is possible to reduce the data size. Examples of a compression technique used here include, but not limited to, Huffman coding-based data compression, joint photographic experts group (JPEG)-formatted compression, and compression based on run length coding architectures.

Compressing the regional image data makes it possible to output the required data to the workpiece inspection apparatus 100 in the form of the data less in size than the pixel bit data in the embodiment 1. Reducing the data size in turn enables acceleration of data communication. Alternatively it is possible to downsize the data distributor circuit 308.

At the data distribution step S108, the data distributor 308 sends the compressed regional image data from the external I/F 312 to comparator circuit 108 while letting a test region be synchronized with the measured data and reference data in a way fit to the inspection speed of the workpiece inspection apparatus 100.

At the regional image data input step S110, the compressed regional image data is input via external I/F 142 to comparator circuit 108. For example, LAN is used for interconnection between the inspection apparatus 100 and the assistant 300. In particular, in order to speed up data communications therebetween, it is preferable to employ gigabit LAN using an optical cable or else, as stated supra.

At data recovery step S113, the data recovery processor circuit 146 reads the compressed regional image data as input to external I/F 142. Then, recover the read data on a real time basis. Next, send the recovered data to memory 306.

In terms of the storage step (S114), optical image acquisition step (S122), data distribution step (S124), storage step (S126), design pattern input step (S142), pattern expansion step (S146), filtering step (S148), data distribution step (S150), storage step (S152) and comparison step (S160), this embodiment is similar to the embodiment 1, so their explanations are omitted.

By compressing the regional image data in the way stated above, it is possible to reduce the data size to smaller than the regional image data of pixel bit data. This makes it possible to increase the communication rate, thereby enabling prevention of its delay relative to the processing speed of workpiece inspection apparatus 100.

It is also preferable to apply this embodiment to the die-to-die inspection shown in the embodiment 2.

Figure 20:
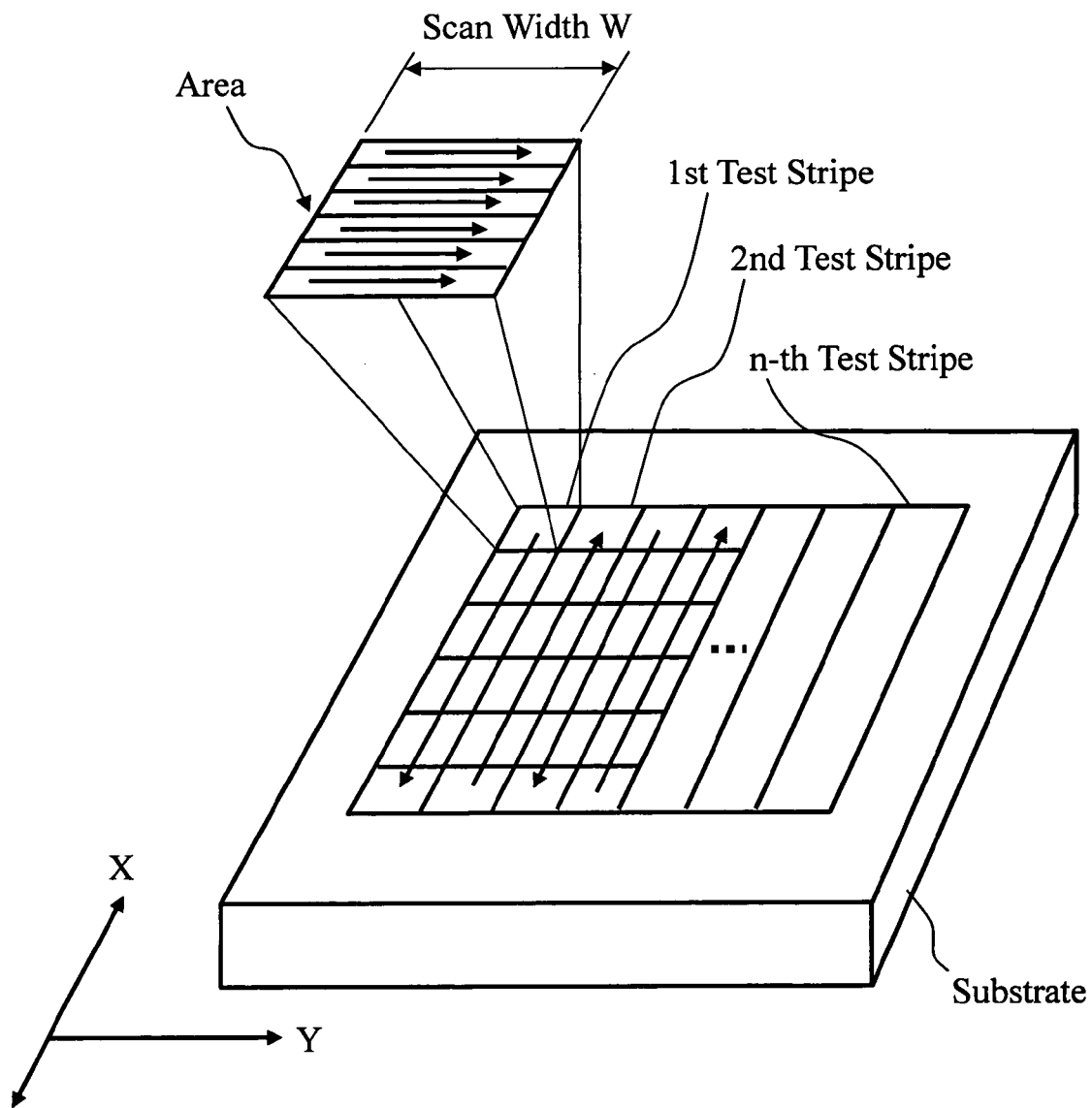
FIG. 20 is a diagram for explanation of another optical image acquisition technique.

FIG. 20 is a diagram for explanation of another optical image acquisition technique. Although the arrangement of FIG. 2 uses the PD array 105 for simultaneous incoming radiation of a specified number of pixels (e.g., 2,048 pixels) having the scan width W, the invention is not limited thereto and may alternatively employ a scheme for acquiring 2D images in units of areas with a prespecified size, by scanning a laser beam using a laser scan optical device (not shown) in the Y direction upon every detection of a fixed pitch of movement at a laser interferometer while sending the XYθ table 102 in the X direction at a constant speed and then detecting transmitted light in a way shown in FIG. 20.

As apparent from the foregoing, according to at least one of the above-stated embodiments, it is possible to input the regional image data from outside. This makes it possible to prevent excessive increase in complexity, cost increase and unwanted extension of development time period of the inspection apparatus otherwise occurring due to improvements in the currently available inspection apparatus. It is also possible by the use of the regional image data to lower the risk of misjudgment as pseudo-defects heretofore. This makes it possible to preclude the redoing of inspection, thereby enhancing the usability of the apparatus. It is also possible to improve the defect inspection accuracy for high precision-required patterns.

System elements which are expressed by the terms "circuits" or "steps" in the description above may be arranged by computer-executable software programs. When the need arises, these may alternatively be implemented not only by software programs but also by use of hardware and software combinations. Similar results are also obtainable by designing them in a combination with firmware. In the case of the arrangement using programs, the programs are prestored in nondestructive recording media, such as magnetic disks, magnetic tapes, floppy disks (FDs), read-only memories (ROMs) or equivalents thereto. For example, those circuits making up the arithmetic control unit in the workpiece inspection apparatus 100—namely, the table control circuit 114, expander circuit 111, reference circuit 112, data distributor circuit 140, comparator circuit 108, pixel bit expander circuit 144, data recovery processor circuit 146, etc.—may be configured from electrical circuitry or alternatively realized in the form of software programs capable of being executed by the control computer 110. Still alternatively, these circuits may be implemented in the form of combinations of electrical circuitry and software programs. The same goes with the circuits in the assistant device 300, i.e., the data converter circuits 304 and 324, data compressor circuit 305, data distributor circuit 308, and distribution controller circuit 310.

While this invention has been particularly shown and described with reference to specific embodiments, the invention should not exclusively be limited thereto. For instance, each embodiment stated supra may be designed to use reflected light in place of the transmitted light or alternatively employ both the transmitted light and reflected light at a time.

Additionally, although detailed explanations are omitted as to those components which are not specifically required for the description of this invention, such as device configuration and control schemes or else, it is possible to selectively use any required device configurations and control schemes on a case-by-case basis.

It should be appreciated that for miscellaneous matters, any variants of the workpiece inspection apparatus assisting device, workpiece inspection methodology and software programs for use therein are construed to be involved in the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assisting device of a workpiece inspection apparatus comprising:
    a regional image data conversion unit configured to be input region data indicative of specified regions of a workpiece with a pattern formed thereon to be tested and convert the region data to regional image data;
    a data distribution processing unit configured to distribute said regional image data to said workpiece inspection apparatus, which is external to said assisting device, in conformity with an inspection processing speed of the workpiece inspection apparatus so that the workpiece inspection apparatus performs pattern defect inspection by comparing optical image data of the workpiece to specified reference image data using respective decision thresholds determined based on said regional image data corresponding to the specified regions being compared; and
    a compression data conversion unit configured to convert said regional image data to a compressed data thereof,
    wherein said data distribution processing unit is configured to distribute said compressed data to said workpiece inspection apparatus.

2. An assisting device of a workpiece inspection apparatus comprising:
    a region data conversion unit configured to be input a first region data indicative of specified regions of a workpiece with a pattern formed thereon to be tested and convert the first region data to a second region data being less in information amount than said first region data;
    a data distribution processing unit configured to distribute said second region data to said workpiece inspection apparatus, which is external to said assisting device, in conformity with an inspection processing speed of the workpiece inspection apparatus so that the workpiece inspection apparatus performs pattern defect inspection by comparing optical image data of said workpiece to specified reference image data using respective decision thresholds determined based on said second region data corresponding to the specified regions being compared; and
    a compression data conversion unit configured to convert said second regional image data to a compressed data thereof,
    wherein said data distribution processing unit is configured to distribute said compressed data to said workpiece inspection apparatus.

3. A readable recording medium storing a program for causing a computer to execute a procedure comprising:
    a first storage process for storing in a first storage device design pattern data of pattern formation of a workpiece with a pattern formed thereon to be tested;
    an input process for inputting, from an external device, regional image data created based on region data indicative of specified regions of said workpiece;
    a second storage process for storing the input regional image data in a second storage device;
    a design image data creation process for making design image data based on the design pattern data stored in said first storage device;
    an optical image data input process for inputting optical image data of said workpiece;
    a third storage process for storing the input optical image data in a third storage device;
    a comparison process for using said regional image data to perform comparison of said design image data and said optical image data; and
    an output process for outputting a comparison result of the comparison process.

4. The readable recording medium according to claim 3, wherein said comparison process is performed using respective decision thresholds determined based on said regional image data corresponding to the specified regions being compared.

* * * * *